United States Patent
Silber et al.

(10) Patent No.: US 6,987,876 B2
(45) Date of Patent: Jan. 17, 2006

(54) SYSTEM AND METHODS FOR DETERMINING THE SETTINGS OF MULTIPLE LIGHT SOURCES IN A VISION SYSTEM

(75) Inventors: Andrew D. Silber, Kirkland, WA (US); Richard M. Wasserman, Redmond, WA (US)

(73) Assignee: Mitutoyo Corporation, Kawasaki (JP)

( * ) Notice: Subject to any disclaimer, the term of this patent is extended or adjusted under 35 U.S.C. 154(b) by 650 days.

(21) Appl. No.: 09/921,886

(22) Filed: Aug. 6, 2001

(65) Prior Publication Data

US 2002/0076096 A1 Jun. 20, 2002

Related U.S. Application Data

(63) Continuation-in-part of application No. 09/736,187, filed on Dec. 15, 2000.

(51) Int. Cl.
 *G06K 9/00* (2006.01)
(52) U.S. Cl. .................................. 382/152; 250/205
(58) Field of Classification Search ................ 382/141, 382/152, 295, 279; 348/86, 92, 131, 371, 348/125; 700/95; 702/34; 250/205, 201.1, 250/216, 208.1, 204; 315/151
See application file for complete search history.

(56) References Cited

U.S. PATENT DOCUMENTS

| | | | |
|---|---|---|---|
| 5,015,053 A * | 5/1991 | Johnson | 385/2 |
| 5,046,847 A * | 9/1991 | Nakata et al. | 356/338 |
| 5,482,801 A * | 1/1996 | Smith et al. | 430/5 |
| 5,519,496 A * | 5/1996 | Borgert et al. | 356/394 |
| 5,753,903 A * | 5/1998 | Mahaney | 250/205 |
| 6,207,946 B1 * | 3/2001 | Jusoh et al. | 250/208.1 |
| 6,303,916 B1 * | 10/2001 | Gladnick | 250/205 |
| 6,627,863 B2 * | 9/2003 | Wasserman | 250/205 |
| 6,677,948 B1 * | 1/2004 | Wasserman et al. | 345/428 |
| 2002/0076096 A1 * | 6/2002 | Silber et al. | 382/152 |
| 2003/0110610 A1 * | 6/2003 | Duquette et al. | 29/407.09 |
| 2004/0053143 A1 * | 3/2004 | Sandstrom | 430/5 |
| 2004/0066964 A1 * | 4/2004 | Neubauer et al. | 382/152 |
| 2004/0136588 A1 * | 7/2004 | Saeki | 382/152 |
| 2004/0151364 A1 * | 8/2004 | Kenneway et al. | 382/152 |
| 2005/0002555 A1 * | 1/2005 | Kumiya et al. | 382/153 |

(Continued)

FOREIGN PATENT DOCUMENTS

JP 61-105582 5/1986

(Continued)

OTHER PUBLICATIONS

U.S. Appl. No. 09/736,187, filed Dec. 15, 2000, Wasserman.

(Continued)

*Primary Examiner*—Daniel Miriam
*Assistant Examiner*—Barry Choobin
(74) *Attorney, Agent, or Firm*—Oliff & Berridge, PLC

(57) ABSTRACT

Systems and methods where a lighting configuration of a vision system is determined using a controllable lighting system and at least one image evaluation tool. The lighting configuration is usable to obtain a desired inspection image of at least one feature of a workpiece Base images are obtained using actual illumination settings of the controllable lighting system. Simulated or synthetic sets image results are generated, based on base images and synthetic lighting configurations. The synthetic lighting configurations include at least one illumination setting which is different from the actual illumination settings used to obtain one or more component base images. A best actual or synthetic lighting configuration is chosen based on the best corresponding set of image results.

30 Claims, 15 Drawing Sheets

U.S. PATENT DOCUMENTS

| | | | |
|---|---|---|---|
| 2005/0018179 A1* | 1/2005 | Bevis et al. | 356/237.1 |
| 2005/0041852 A1* | 2/2005 | Schwarz et al. | 382/152 |
| 2005/0094867 A1* | 5/2005 | Jones et al. | 382/152 |
| 2005/0109959 A1* | 5/2005 | Wasserman et al. | 250/559.19 |
| 2005/0151978 A1* | 7/2005 | Nakamura et al. | 356/602 |

FOREIGN PATENT DOCUMENTS

| | | |
|---|---|---|
| JP | 62-91993 | 4/1987 |
| JP | 2-254419 | 10/1990 |
| JP | 4-265946 | 9/1992 |
| JP | 5-11261 | 1/1993 |
| JP | 5-19294 | 1/1993 |
| JP | 5-333373 | 12/1993 |
| JP | 9-325363 | 12/1997 |
| JP | 10-26771 | 1/1998 |
| JP | 10-232408 | 9/1998 |

OTHER PUBLICATIONS

Leon, F. Puente, "Enhanced imaging by fusion of illumination series", Proc. of the European Symposium on Lasers and Optics in Manufacturing, Munich, FR Germany, Jun. 20, 1997, pp. 1-12.

* cited by examiner

SYSTEM AND METHODS FOR DETERMINING THE SETTINGS OF MULTIPLE LIGHT SOURCES IN A VISION SYSTEM

This is a Continuation-in-part of application Ser. No. 09/736,187 filed Dec. 15, 2000. The entire disclosure of the prior application is hereby incorporated by reference herein in its entirety.

BACKGROUND OF THE INVENTION

1. Field of Invention

This invention relates to lighting systems for vision systems.

2. Description of Related Art

The light output of any device is a function of many variables. Some of the variables include the instantaneous driving current, the age of the device, the ambient temperature, whether there is any dirt or residue on the light source, the performance history of the device, etc. Machine vision instrument systems typically analyze features or objects within their field of view using methods which may determine, among other things, the location of edges of a feature on an object or the contrast within the region of interest where the features or objects may be found. To some degree, this determination is affected by the character of incident light or transmitted light.

A machine vision system programmer or operator often wishes to illuminate a workpiece to achieve a specific image characteristic. The image characteristic may be a specific average gray level value in a region of interest or a goal such as to maximize the difference in average gray level between various regions of interest, or to maximize a gradient within a region of interest. More generally, the desired characteristic may be a complex series of goals defined across an image scan line.

In many applications, the relationship between the imaging subsystem and the workpiece under inspection is predictable. In such applications, the predictability of the situation allows a simple form of reproducible lighting control. As illustrated in U.S. Pat. No. 5,753,903 to Mahaney, for example, closed-loop control systems are used to ensure that the output light intensity of a light source of a machine vision system was driven to a particular command level. These conventional closed-loop control systems prevent the output light intensity from drifting from the desired output light intensity due to variations in the instantaneous drive current, the age of the light source, the ambient temperature, or the like. Accordingly, it is possible to determine a light intensity setting or level for a single, spatially fixed illumination source and an actual workpiece. However, even when such a simple form of reproducible lighting control is possible, performing a search for an optimal light source setting can become problematic because each of the steps of light adjustment, acquisition of each video frame, and evaluation of each video frame requires a finite period of time. In particular, common halogen lights require a lengthy period of time to stabilize their output after their current drive is altered. Thus, although there are several conventional approaches to choose a satisfactory light intensity setting for a given workpiece and a single fixed light source, there may be some associated delays which reduce the available throughput of the associated vision system.

In U.S. application Ser. No. 09/736,187, which is incorporated herein by reference, discloses a vision system and method for determining a prescribed illumination setting for a vision system that has a controllable lighting system. The prescribed illumination setting is usable to acquire a desired image that has a desired image characteristic in a region of interest. As disclosed in the '187 application, the method comprises obtaining a plurality of base images of at least the region of interest, where each base image comprises an actual image corresponding to an actual illumination setting, and determining, for at least the region of interest, a synthetic image based on a current prospective illumination setting and at least one of the base images. Then, the process evaluates whether the synthetic image corresponds to a desired image. If the synthetic image result does not correspond to the desired image, the process modifies the current prospective illumination setting. The process then repeats the determining, evaluating and modifying steps until at least one synthetic image corresponds to the desired image.

SUMMARY OF THE INVENTION

However, in some cases, the synthetic image may not accurately represent the image obtained using the lighting settings determined based on the synthetic image. Additionally, in many instances, although linear vision systems have great flexibility on how to light an object, there are no tools to help a user choose the best lighting solution. For example, if the user wishes to automatically create a part program using a computer aided design (CAD) file data, there is generally sufficient CAD information to move the stage to proper coordinates to successfully perform an auto-focus process. However, there may not be enough information from the CAD file data to achieve desired lighting configurations.

Thus, considering the problems of throughput, quantitative accuracy in the final image, and the ability to adapt to a variety of unpredictable workpiece features and configurations, conventional methods do not offer a complete solution for determining the most desirable lighting configuration for a feature or region of interest. This is particularly true when using multiple illumination sources. This problem is particularly significant in the design of a fully automated off-line part program generation system.

Thus, there is a need for systems and methods for precisely acquiring an image regardless of the overhead, or time consumption, involved, that achieves the desired image characteristics. Such a process could implement the use of a standard or novel search technique to search the problem landscape for the desired lighting configuration, that is, the lighting settings for each of the various lighting sources. Currently, the main problem associated with conducting a trial and error search for a desirable combination of multiple light source settings is the enormous number of possible configurations and the overhead associated with changing the output power of each lamp and waiting for the trial images to be acquired and evaluated.

This invention provides systems and methods that allow a vision system to search for a desirable combination of multiple light source settings in a relatively short time.

This invention separately provides systems and methods that allow a vision system to identify a most desirable combination of multiple light source settings for any of a variety of feature analyses that are reliable, robust, and readily adaptable.

This invention separately provides systems and methods that simulate the effects of combinations of multiple light sources on an object to be viewed.

This invention provides systems and methods that combine collected data from multiple images acquired by a vision system and synthesizes additional images in order to determine a desirable lighting configuration.

This invention further provides systems and methods that extract characteristics of an image that represent a quality of a particular lighting configuration.

This invention further provides systems and methods that assign measurement scores indicative of the quality of extracted characteristics so that the scores may be analyzed.

This invention further provides systems and methods that analyze the extracted characteristics through the measurement scores in order to determine a best lighting configuration.

This invention further provides systems and methods that ranks the data extracted through the characteristic extraction process in order to analyze the data through the use of a classifier so that a best lighting configuration can be determined.

This invention further provides systems and methods that choose or configure a classifier according to the expected or actual quality or reliability of an image characteristic so that a best actual lighting configuration can be determined with increased speed or reliability.

This invention further provides systems and methods that determine a best actual lighting configuration by determining whether a determined image is a base image or synthetic, and if the determined image is a synthetic image, further analyzing the effects of multiple light sources on the object prior to determining the best actual lighting configuration.

This invention further provides systems and methods that use a determined best actual or synthetic image to set lighting vectors of a vision system.

In various exemplary embodiments of the systems and methods according to this invention, a lighting configuration of a vision system is determined through the use of a controllable lighting system and at least one image evaluation system or method. The lighting configuration is used to obtain a desired inspection image of at least one feature of a workpiece by identifying with a feature to be inspected, and then obtaining a plurality of base images of the feature to be inspected. Base images are obtained using an actual lighting configuration of the controllable lighting system. Simulated or synthetic images of the inspected feature are generated, based on one or more of the base images. In these simulated or synthetic images, at least one lighting configuration setting is different from the actual lighting configurations used to obtain one or more of the one or more component base images. The image evaluation system or method is then applied to at least one base image and to at least one simulated image to evaluate the images and determine a best or adequate actual or synthetic image.

Start-up parameters usable to begin acquiring the base images can be based on a CAD data file. Then base image data is acquired and synthesized image data is generated and stored. One or more characteristics are then analyzed to determine one or more measurements for each base and synthetic image. Once the desired characteristics are analyzed, one or more measurement scores determined for each base and synthetic image are compared. The one or more measurement scores reflect the quality of each base or synthesized lighting solution in illuminating the part for the desired features.

The desired characteristics are analyzed to determine measurement scores or image metrics for all lighting configurations. Such image metrics can include, for example, ranking transition scores, position scores, shape scores, edge scores and/or a standard deviation score. For example, in various exemplary embodiments, the user can define, as the measurement scores or image metrics, a shape score that represents a deviation between a best fit line and an actual position, or a position score that represents deviations between detected positions and expected positions. A classifier is applied to the measurement scores or image metrics to identify a best one of the base and synthetic images.

In various embodiments, once this best image is determined, if the best image is a synthetic image, a new series of actual images is acquired by varying the lighting configuration in small increments around the lighting configuration used to generate the best synthetic image from the original base images. These new actual images are then analyzed in the same way to determine a final best image from the new series of actual images.

In contrast to the previously discussed conventional methods, in various exemplary embodiments of the systems and methods according to this invention, slow hardware trial-and-error procedures are reduced, minimized or avoided completely. The previously known methods acquired an extensive actual image series to select a best actual image and/or lighting configuration. This final best image and/or lighting configuration in these conventional methods can be no better than the best previous image in a series of images which is limited due to lighting system response times, vision system throughput rates, and overall time constraints. In contrast to these conventional methods, the systems and methods according to this invention acquire a relatively limited set of actual images and create a series of synthetic images to very rapidly determine a best, near best, or adequate lighting configuration from a very large set of potential lighting configurations. A best, near best, or adequate lighting configuration corresponding to a synthetic image is then chosen or rapidly refined or confirmed based on one or more actual images.

These and other features and advantages of this invention are described in, or are apparent from, the following detailed description of various exemplary embodiments of the systems and methods according to this invention.

BRIEF DESCRIPTION OF THE DRAWINGS

Various exemplary embodiments of this invention will be described in detail, with reference to the following figures, wherein.

DETAILED DESCRIPTION OF PREFERRED EMBODIMENTS

Figure 1:
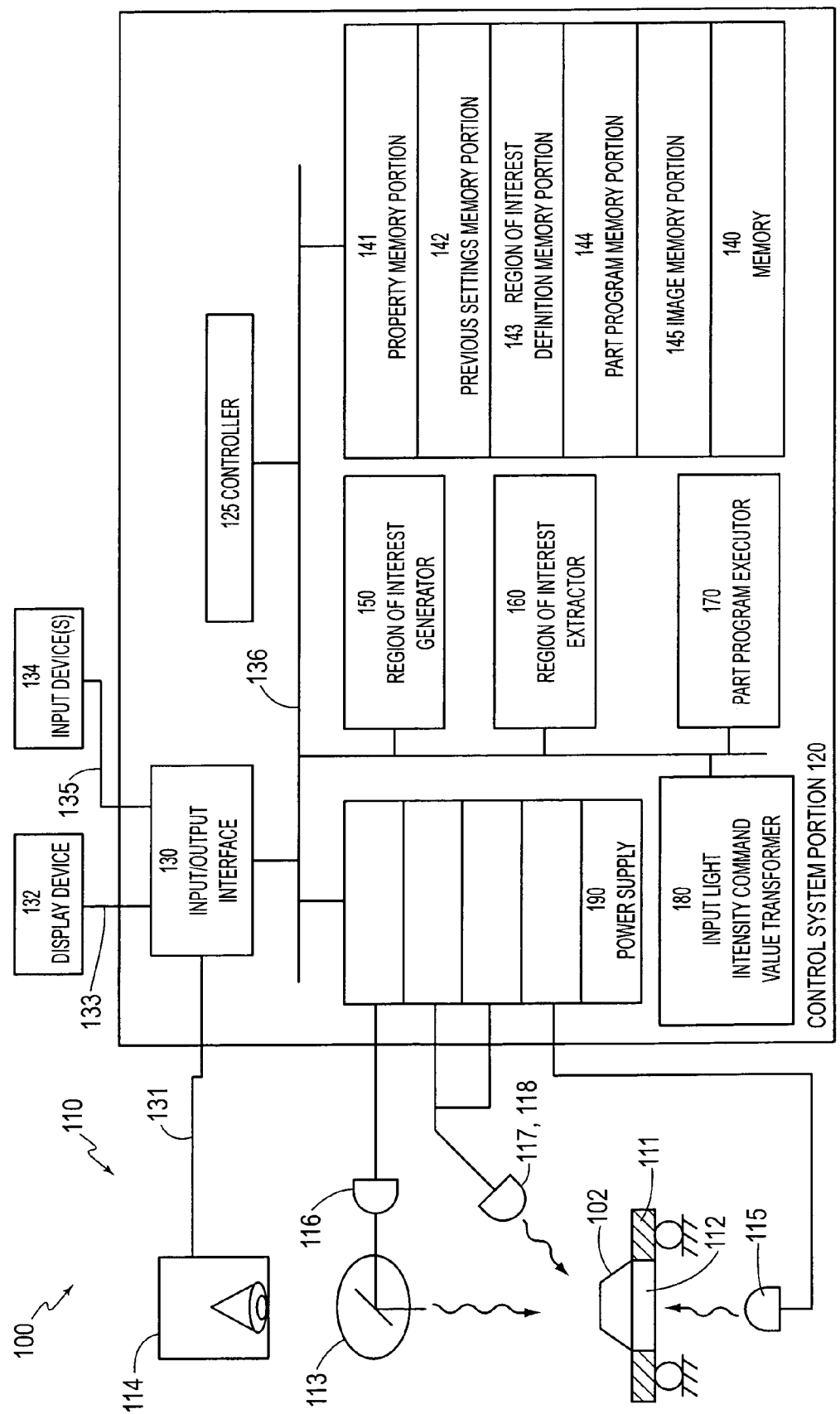
FIG. 1 a block diagram of one exemplary embodiment of a vision system having a light intensity control system according to this invention.

For simplicity and clarification, the operating principles, and design factors of various exemplary embodiments of the systems and methods according to this invention are explained with reference to one exemplary embodiment of a vision system 100, as shown in FIG. 1. The basic explanation of the operation of the vision system shown in FIG. 1 is applicable for the understanding and design of any vision system that incorporates this invention. Although the systems and methods of this invention are described in conjunction with this specific vision system 100, the systems and methods according to this invention can be used with any other known or later-developed vision system.

FIG. 1 shows a vision system 100. As shown in FIG. 1, the vision system 100 includes a vision system components portion 110 and a control portion 120. The control portion 120 includes elements, including a property memory portion 141 described below, which constitute a light intensity control system usable in accordance with this invention. The control portion 120 further includes elements, including a part program executor and/or generator 170 described below, which constitute a control instruction generation system usable in accordance with this invention.

The vision system components portion 110 includes a stage 111 having a central transparent portion 112. A part 102 to be imaged using the vision system 100 is placed on the stage 111. The light from a number of different light sources 115–118 passes through a lens system 113 after illuminating the part 102, and possibly before illuminating the part 102, and is gathered by a camera system 114 to generate an image of the part 102. The light sources used to illuminate the part 102 include a stage light 115, a coaxial light 116, and/or a surface light, such as a ring light 117 or a programmable ring light (PRL) 118.

Each of the light sources 115–118, separately, or in combination, constitute a controllable lighting system. It should be appreciated that any one of the various light sources 115–118 described above can include a plurality of different colored light sources. That is, for example, the stage light 115 can include a red light source, a green light source and a blue light source. Each of the red, blue and green light sources of the stage light 115 will be separately driven by the power source 190, and may be considered as a separate light source in various embodiments of the systems and methods according to this invention.

It should also be appreciated that, if a focusable light source or a movable light source such as a programmable ring light is included in the controllable lighting system, then, in various alternative exemplary embodiments of the systems and methods according to this invention, various discrete positions of the focusing element or discrete positions of the movable light source may be treated as separate light sources, in order to identify the most desirable lighting focus, or movable light position. Any separately controllable portions of a programmable ring light may also be regarded as separate sources. It should be appreciated that any combination of known or later developed single-color, multi-color, fixed, moveable and/or focusable light sources may be used in conjunction with this invention without departing from the spirit and scope of the invention.

In general, all of the previously described controllable aspects of the various light sources included in the controllable lighting system are described by, and/or governed by a lighting configuration. The lighting configuration describes and/or determines the particular illumination configuration which is used to capture an associated image. In various exemplary embodiments, the illuminating setting may be represented as a lighting vector.

The image captured by the camera is output on a signal line 131 to the control portion 120. As shown in FIG. 1, the control portion 120 includes a controller 125, an input/output interface 130, a memory 140, a part program executor and/or generator 170, an input light intensity command value transformer 180, and a power supply 190, each interconnected either by a data/control bus 136 or by direct connections between the various elements. The signal line 131 from the camera system 114 is connected to the input/output interface 130. A display 132 can also be connected over a signal line 133 to the input/output interface 130. Similarly, one or more input devices 134 can be connected over one or more signal lines 135 to the input/output interface 130. The display 132 and the one or more input devices 134 can be used to view, create and modify part programs, to view the images captured by the camera system 114 and/or to directly control the vision system components 110. However, it should be appreciated that, in a fully automated system having a predefined part program, the display 132 and/or the one or more input devices 134, and the corresponding signal lines 133 and/or 135 may be omitted.

Figure 3:
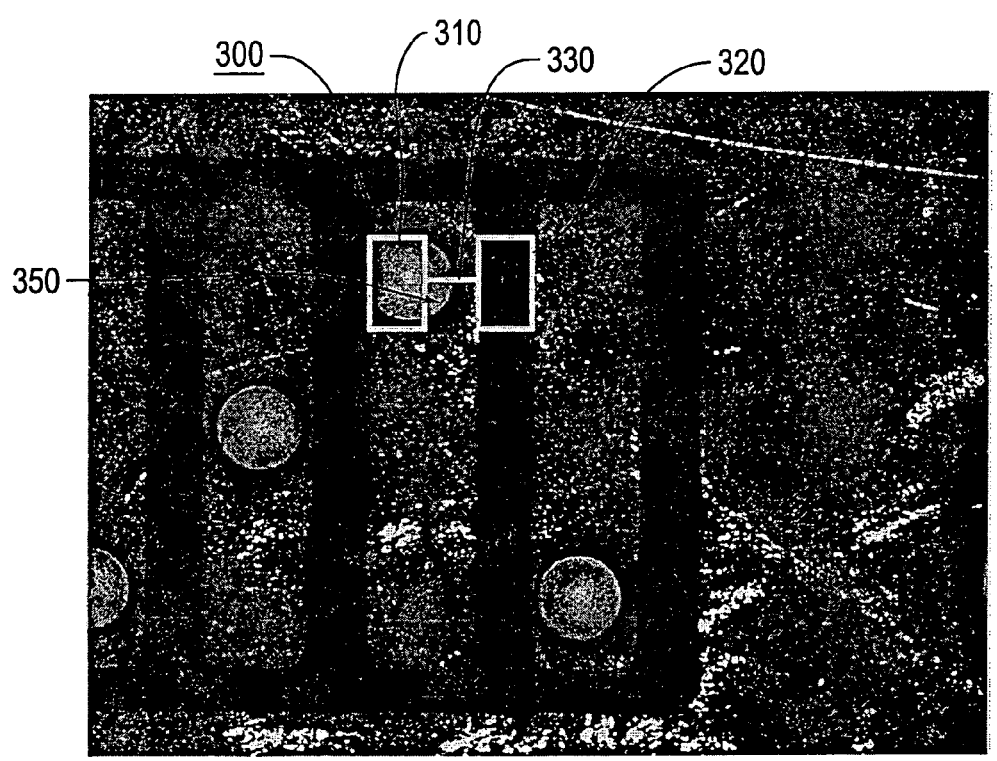
FIG. 3 illustrates an exemplary image and one exemplary embodiment of an image quality tool usable in conjunction with various embodiments of the systems and methods according to this invention.

As part of the memory 140, the part program memory portion 144 stores one or more part programs used to control the operation of the vision system 100 for particular types of parts. The image memory portion 145 stores images captured using the camera system 114 when operating the vision system 100. Furthermore, a region of interest definition memory portion 143 contains data defining the location of one or more regions of interest within the captured image, including the parameters of a measurement tool, such as the image quality tool 300 shown in FIG. 3. The image quality tool 300 shown in FIG. 3 is described in greater detail below.

In the vision system 100, a previous setting memory portion 142 stores previous settings for the various light sources 115–118 that were in place prior to the part program executor and/or generator 170 adjusting one or more of the light sources 115–118. A property memory portion 141 stores data identifying the light source or sources that will be adjusted to obtain the desired image quality, data defining the operation mode for operating the various light sources 115–118, data defining the image quality that is to be used as the metric for determining whether the identified light source(s) to be used to illuminate the part 102 need further adjusting, and data defining whether the image data in the regions of interest is to be filtered.

It should be appreciated that the vision system 100 in accordance with this invention can include circuits, software programs, coding and the like that perform the operations, routines and sub-routines disclosed in this application. One skilled in the art will be familiar with the circuits, software programs and/or coding required to implement the methods in accordance with this claimed invention. Moreover, it should be appreciated that the foregoing description of the vision system 100 used with this invention generally describes an automatic program operation. However, the vision system 100 used with this invention may also operate substantially the same when the illumination commands are issued manually through one or more of the one or more input devices 134 during manual or stepwise operation of the vision system 100. Furthermore, although the vision system 100 is capable of adapting various parameters, this following discussion assumes that the configuration of the imaging system and the workpiece under inspection is already known or predictable. In addition, any focus conditions are assumed to have been met, and the position and orientation of the lighting sources relative to the object or part 102 are known.

When a machine vision system programmer wishes to illuminate a specific workpiece mounted on the stage 111, such as the part 102, to capture an image of that workpiece, where the captured image has one or more specific image characteristics, the programmer would operate the vision system 100 to create a part program and to typically select and define a number of specific image measurement or analysis tools which govern particular image analysis tasks. One exemplary image analysis tool, described for purposes of illustration herein, is the image quality tool 300 shown in FIG. 3, described in greater detail below.

More generally, when a measurement tool is set up by the operator during part programming, the scan line or area of the captured image used to determine the required measured value is defined in the tool. In particular, the part program will cause the vision system 100 to manipulate the stage 111 and/or the camera system 114 such that a particular portion of the part 102 is within the field of view of the camera system 114 and illuminated using a desired lighting vector or lighting configuration, and at a desired focus state to obtain one or more desired image characteristics. The part program executor and/or generator 170 would then, under the control of the controller 125, command the camera system 114 to capture an image of the part 102 using the desired lighting vector and focus state and output the captured image to the control system 120. The control system 120 will then, under the control of the controller 125, input the captured image through the input/output interface 130 and store the captured image in the captured image storage portion 145 of the memory 140. The controller 125 could then display the captured image on the display device 132.

Figure 2:
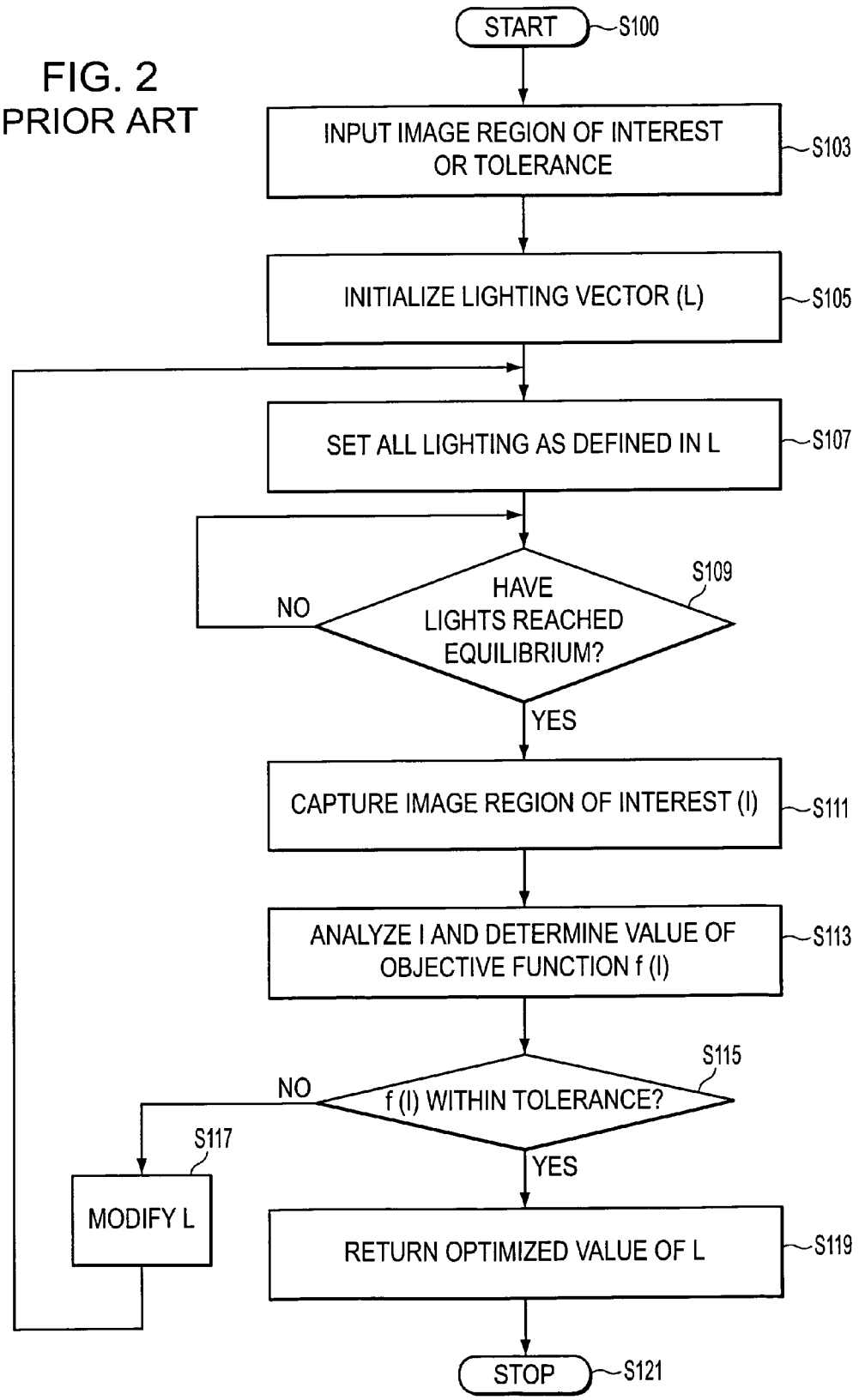
FIG. 2 is a flowchart outlining a conventional method for determining multi-channel lighting settings.

In order to determine the one or more lighting conditions, i.e., the lighting vector or lighting configuration, that allow an image of the part 102 to be captured such that the captured image has the one or more desired image characteristics using the part program in the vision system 100, it is conventional to vary the actual lighting conditions, either based on user experience or by systematic or quasi-systematic trial and error, until the desired image characteristics are obtained. FIG. 2 is a flowchart outlining a conventional method for determining multi-channel lighting settings that allow an image having the desired image characteristics to be captured. In this conventional method, actual base image data is analyzed for each set of lighting settings.

After beginning in step S100, operation continues to step S103, where an image region of interest and/or an image characteristic tolerance value is defined. A tolerance value would indicate the range of image quality values that are acceptable and thus require no further adjustment of the lighting settings of the selected one or more light sources. Next, in step S105, a lighting vector L, i.e., the set of lighting settings for the one or more light sources, is initialized. The lighting vector L contains one entry for each light source, and each entry corresponds to the lighting power output by that light source. As previously discussed, various color sources within a light source, or other separately positioned and controllable sources within a light source, may be regarded as separate light sources. Then, in step S107, the lighting power outputs of the light sources of the vision system 100 are set to the level defined in the lighting vector L. Operation then continues to step S109.

In step S109, a determination is made whether the light sources have reached a steady state. This is done, for example, with halogen light sources, which require a period of time to stabilize their illumination intensity output after the drive current is altered. If, in step S109, the light sources have not all reached a steady state, operation jumps back to step S109 until all of the light sources have reached steady state. Once all of the light sources have reached steady state, operation continues to step S111, where an image containing the image region of interest I is captured. Then, in step S113, the region of interest I is analyzed to determine a value of an objective function $f(I)$. In various exemplary embodiments, the resulting value is a scalar output. Next, in step S115, a determination is made whether or not the objective function $f(I)$ is within the selected, or alternatively within a predetermined, tolerance. If the objective function $f(I)$ is not within the selected or predetermined tolerance, operation jumps to step S119. Otherwise, operation continues to step S117, where the lighting vector L is modified. Control then returns to step S107.

In contrast, in step S119, the current lighting vector L is returned as a lighting vector that is able to illuminate the part 102 such that an image having the desired image characteristics can be captured. Then, in step S121, the method ends.

In contrast to the foregoing conventional method based on hardware control adjustments and actual image acquisition, in the systems and methods according to this invention, the one or more lighting conditions that allow the part 102 to be captured with one or more desired image characteristics are determined by varying the lighting conditions in a virtual simulation, and analyzing the simulated, or synthetic, image data.

FIG. 3 illustrates an exemplary image and one exemplary embodiment of an image quality tool 300 usable in conjunction with various embodiments of the systems and methods according to this invention. In particular, the exemplary image quality tool 300 shown in FIG. 3 is a dual area image quality tool, as described in greater detail in co-pending U.S. application Ser. No. 09/484,897, incorporated herein by reference in its entirety. As shown in FIG. 3, the dual area image quality tool 300 includes a first region of interest 310 and a second region of interest 320 connected by a bar 330.

As described in the incorporated 897 application, a user can manually operate a vision machine in training mode. In this training mode the user can manipulate the dual area image quality tool 300 to ensure that the regions of interest 310 and 320 include the proper portions of the captured image and/or to ensure that the bar 330 extends across a critical feature to be measured, such as the edge 350. Once the user is satisfied that the dual area image quality tool 300 is properly positioned, the user establishes a target value for the dual area image quality tool 300. This target value is established, for example, by adjusting the light sources until the user's subjective evaluation of the image quality in the critical region is favorable.

The user then signals the control system 100 to incorporate the current tool parameters into the part program. In response, the part program generator and/or executor 170 generates a part program instruction based on the current state of the dual area image quality tool 300. Then, one or more values corresponding to the image quality or characteristic are determined from the current, subjectively-favored image data. That value then that becomes the stored numerical target reference value that governs the run-time lighting adjustments during future automatic execution of the part program.

However, it should be appreciated that various exemplary embodiments of the systems and methods according to this invention can be used in conjunction with the dual area image quality tools as described in the incorporated 897 application. For example, various embodiments of the systems and methods according to this invention can be used to replace or assist the user during any or all of the operations that adjust the light sources, evaluate when the image quality in the critical region is favorable, establish the target value for the dual area image quality tool 300, and/or signal the control system 100 to incorporate the current tool parameters into the part program. In various exemplary applications, it is desirable to achieve the largest difference in contrast between the first region of interest 310 and the second region of interest 320 or the dual area image quality tool 300. In further exemplary embodiments, it is desirable to minimize the contrast in at least one of the regions of interest. The contrast may be represented by the value of the standard deviation of the pixel intensity values in a region. Thus, the dual area contrast tool 300 is usable to determine a standard deviation score usable in various exemplary embodiments according to the systems and methods of this invention.

Thus, it should be appreciated that various exemplary embodiments of the systems and methods according to this invention can be used to enhance and/or automate not only the dual area image quality tool 300, but a wide variety of other known and/or later-developed image analysis tools, regardless of their apparent operating limitations and/or manual nature in the absence of the systems and methods according to this invention.

Further, it should be appreciated that the potential of various exemplary embodiments of the systems and methods according to this invention for automatic operation, and relatively high-speed execution, allows the systems and methods according to this invention to be implemented at run time, to check and/or adjust for unforeseen conditions such as unexpected ambient lighting conditions, lighting system faults, and process-drift or the like, if appropriate. Such applications of the various exemplary embodiments of the systems and methods according to this invention therefore allow an unprecedented level of reliability and robustness to be achieved, particularly with precision automatic vision systems.

Figure 4:
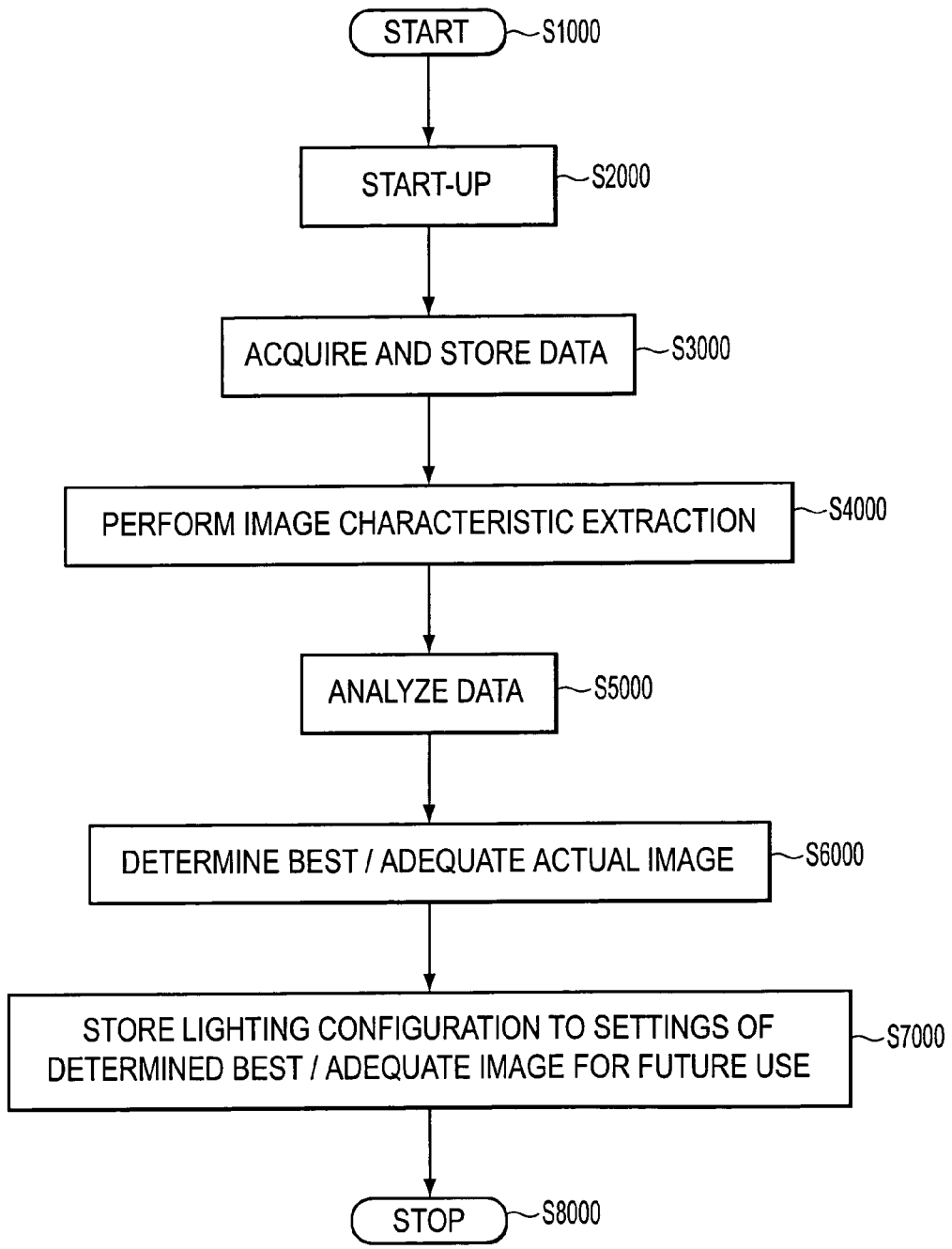
FIG. 4 is a flowchart outlining a first exemplary embodiment of a method for determining multi-channel lighting settings according to this invention.

FIG. 4 is a flowchart outlining a first exemplary embodiment of a method according to this invention that uses both actual image data and synthesized image data to determine the multi-channel lighting settings that allow an image having desired image characteristics to be captured.

After beginning in step S1000, operation continues to step S2000, where a start-up routine is performed and the program for the vision system in FIG. 1 is initialized. During this step, in various exemplary embodiments, the vision system is operable to control over the light sources, including the height of any programmable ring light (PRL), by manual, semi-automatic or automatic means. In the case of manual control, in various exemplary embodiments a lighting tool is open to facilitate user control of the vision system lighting. A more detailed description of the start-up process will be described with reference to FIG. 5. Next, in step S3000, actual or base image data is acquired and stored, and synthetic image data is generated and stored, in the memory. A more detailed description of the base and synthetic image data acquiring and storing process will be described with reference to FIGS. 7–9. Operation then continues to step S4000.

In step S4000, one or more desired image characteristics are extracted or determined from the base and synthetic images. Here, captured and synthesized images are analyzed to extract one or more characteristics related to features and/or regions of interest of the image that are indicative of the quality of a particular lighting solution i.e., lighting vector or lighting configuration. A more detailed description of the image characteristic extraction process will be described with reference to FIG. 10. Next, in step S5000, the extracted characteristics from the base and synthetic images are analyzed. The analysis process will be described in more detail with reference to FIGS. 11–13. Then, in step S6000, in various exemplary embodiments, either a best image or an adequate image is determined based on the analyzed extracted characteristics from the base and synthetic images. The process for selecting the best image will be described in greater detail with reference to FIG. 14. Next, in step S7000, the lighting configuration of the determined best/adequate image is stored for future use to set the various light sources in the vision system when repeating a substantially similar imaging or inspection operation. Finally, in step S8000, operation ends.

It should be appreciated that a simulated image can have a variety of data representations. Furthermore, various evaluations which determine an image characteristic for a particular image, or simulated image, may require only part of the data conventionally expected to constitute a simulated image, or only particular metrics extracted from that data.

Various exemplary embodiments of the systems and methods according to this invention are described herein as generating a simulated image as the basis for an image result which is evaluated. However, it should be appreciated that the image result may be determined from a variety of data representations not generally recognized as a simulated image. Provided that such data representations are usable to provide one or more image results which are usable to determine whether a particular lighting configuration provides a best or adequate image according to the systems and methods of this invention, such data representations are included in the scope of the terms "simulated image" or "synthetic image" or "synthesized image", and thus are within the scope of the systems and methods according to this invention. It should be further appreciated that, in various other exemplary embodiments, depending on the image results to be determined, an objective function, an image characteristic extraction, an image metric or another form of image result, may be determined directly from the base images and a governing lighting vector without needing to represent or generate a simulated image as a recognizable intermediate step.

Figure 5:
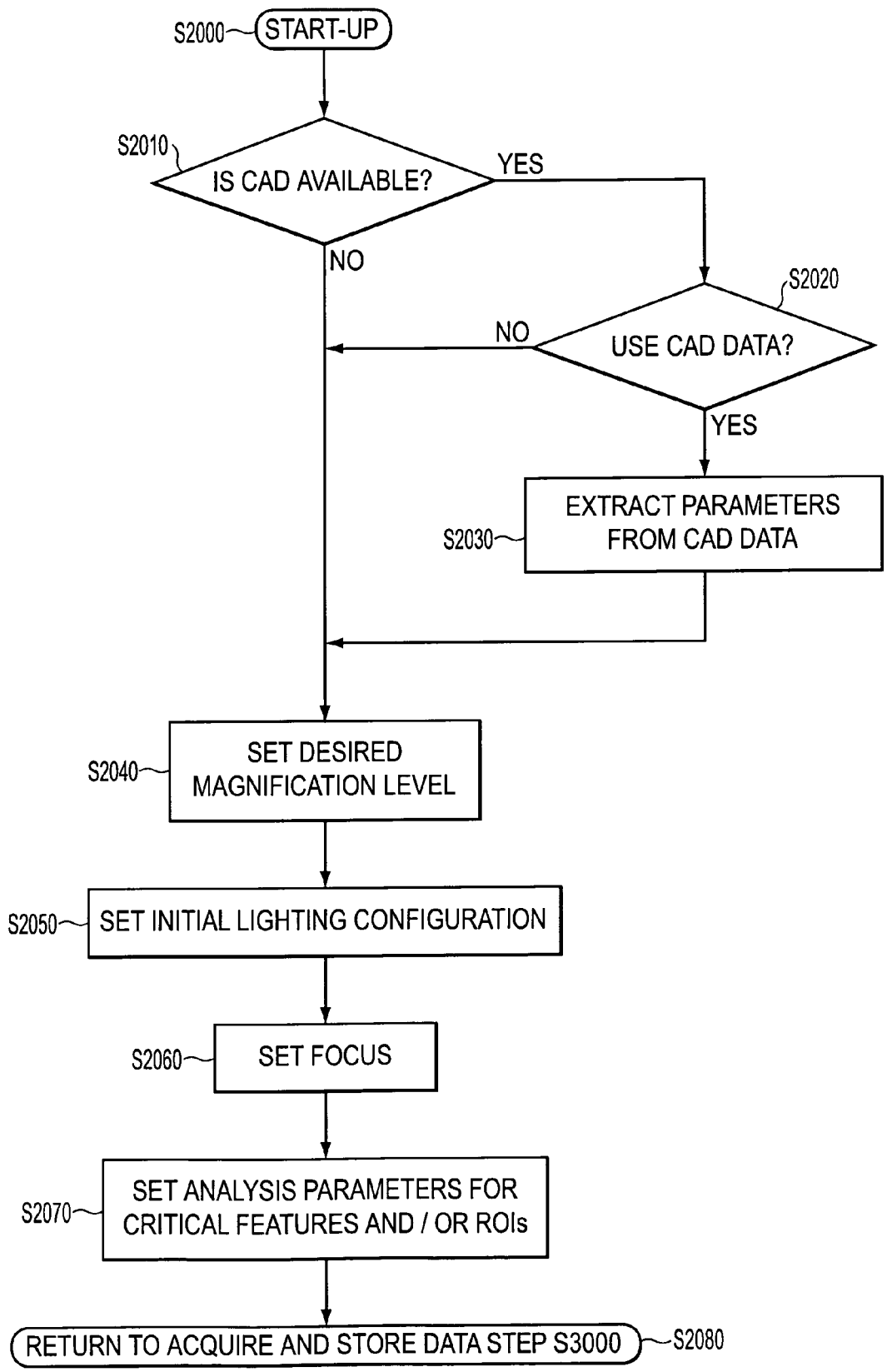
FIG. 5 is a flowchart outlining in greater detail one exemplary embodiment of a method for start-up and initializing the vision system according to this invention.

FIG. 5 is a flowchart outlining in greater detail one exemplary embodiment of the method for starting up and initializing the process for the vision system disclosed in FIG. 1. After beginning in step S2000, operation continues to step S2010, where a determination is made whether computer aided design (CAD) file data is available. If, in step S2010, CAD file data is not available, then operation proceeds to step S2040. Otherwise, in step S2010, if the CAD file data is available, then operation proceeds to step S2020.

In step S2020, since the CAD file data is available, a determination is made whether to use the CAD file data, based on the convenience of use of the CAD data, for example. If the CAD file data will not be used, then operation jumps to step S2040. Otherwise, if the CAD file data will be used, then operation proceeds to step S2030. In step S2030, one or more of the image capture parameters described below with respect to steps S2040–S2070 are determined or extracted from the CAD file data and information representing the vision system configuration. The one or more of the image capture parameters are then used in the one or more corresponding steps S2040–S2070. Operation then continues to step S2040.

In step S2040 a desired magnification level for the system is set by any manual, semi-automatic or automatic method which is compatible with the vision system. Next, in step S2050, an initial lighting configuration for the system is set by any manual, semi-automatic or automatic method which is compatible with the vision system. In various exemplary embodiments, the initial lighting configuration is a reasonable configuration determined by an expert user or an expert program based on the anticipated type of image or image analysis to be performed. In various other exemplary embodiments, the initial lighting configuration is simply a default configuration for the system or for the type of part being imaged. Further considerations related to reasonable lighting configurations are also apparent throughout this description and in the incorporated 187 application.

In step S2060, the image capture system is focused on a relevant region of interest, or a particular feature in such as an edge of the part 102, by any manual, semi-automatic or automatic method which is compatible with the vision system. For example, if the primary purpose of the current operation is to measure an edge location, the system is set to focus on the edge by any manual, semi-automatic or automatic method which is compatible with the vision system. Similarly, if the primary purpose of the current operation is to measure a surface height, then the system is set to focus on a region of the surface.

In step S2070, the primary purpose of the current operation is determined and the analysis parameters are set for the critical features and/or regions of interest corresponding to the current operation. In various exemplary embodiments, the primary purpose of the current operation is determined by the type of image analysis tool selected by an operator or an automatic program that is operating the vision system. Furthermore, in various exemplary embodiments, some or all of the analysis parameters are determined based on the placement and "training" of the selected image analysis tool.

An exemplary process for setting the analysis parameters when the current operation includes analyzing an edge location will be described in greater detail with reference to FIG. 6. Operation then proceeds to step S2080, where operation returns to step S3000.

Figure 6:
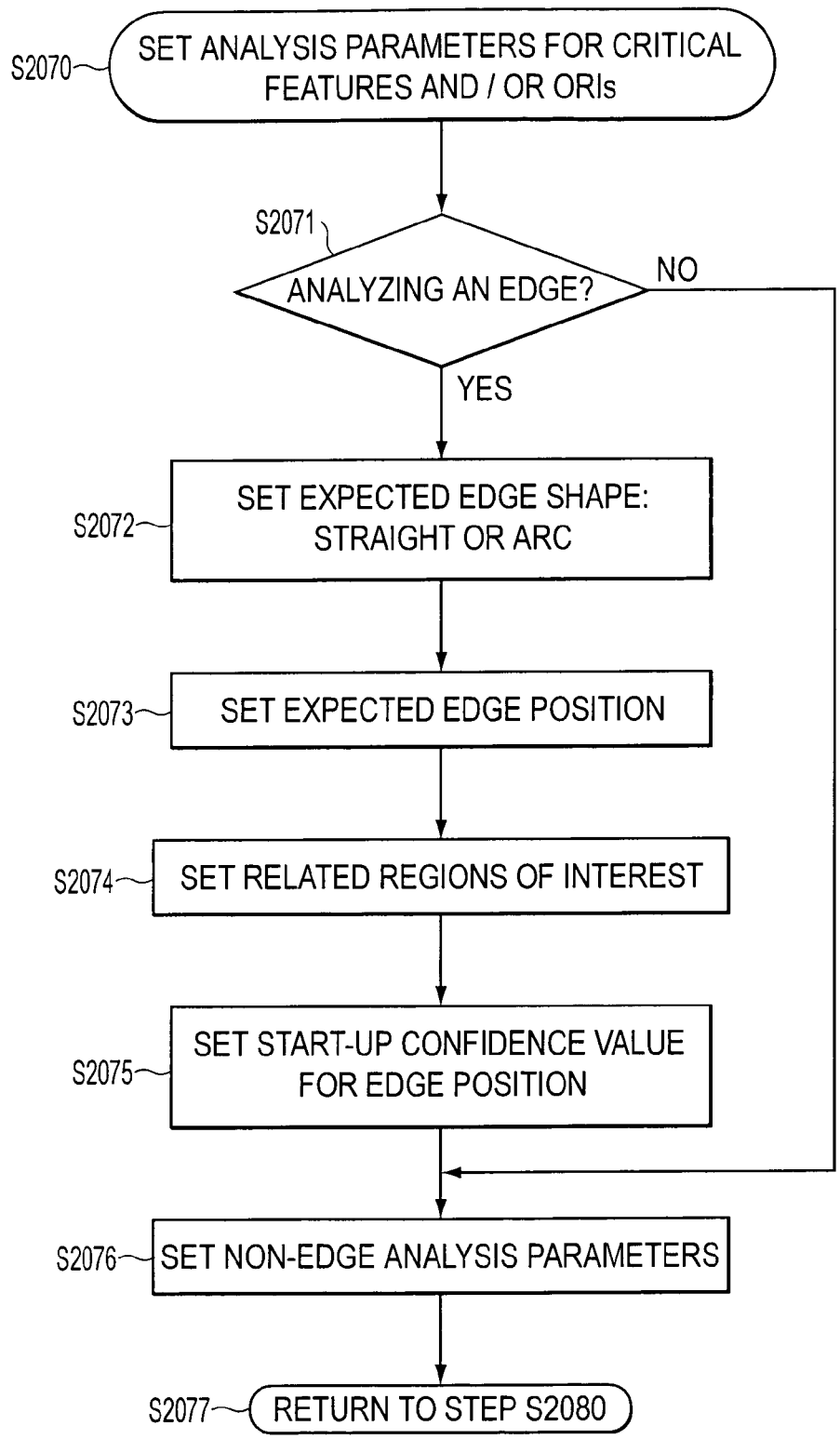
FIG. 6 is a flowchart outlining in greater detail one exemplary embodiment of a method for setting analysis parameters for critical features and/or regions of interest according to this invention.

FIG. 6 is a flowchart outlining in greater detail one exemplary embodiment of a method for setting analysis parameters for critical features and/or regions of interest according to this invention when the current operation includes analyzing an edge location. Beginning in step S2070, operation proceeds to step S2071, where it is determined whether the current operation includes analyzing an edge. If the current operation does not include analyzing an edge, then operation jumps to step S2076. Otherwise, operation proceeds to step S2072.

In step S2072, an indication of the edge shape is set as a straight line or an arc. In various exemplary embodiments, the edge shape is set by the operator of the vision system by input to an edge tool user interface, or by manually or automatically indicating various points along the edge through a suitable user interface and operating the vision system to determine whether a straight line or an arc provides the best fit to the points, or based on the CAD data operations of step S2030. Next, in step S2073, the expected edge location is similarly set by the operator of the vision system by input to an edge tool user interface, or by manually or automatically indicating various points along the edge through a suitable user interface and operating the vision system to determine the location of the line that provides the best fit to the points, or based on the CAD data operations of step S2030. Then, operation proceeds to step S2074.

In step S2074, one or more region of interests adjacent to the edge to the are set. Here, for example, the dual area contrast tool shown in FIG. 3 can be used to define the region of interest. Use of the regions of interest in various exemplary embodiments according the systems and methods of this invention is described in detail further below. Operation then proceeds to step S2075.

In step S2075, a "start-up" confidence value for the edge location is set, if applicable. The confidence value defines whether the labeled edge location is well defined or not and in various exemplary embodiments includes consideration of both fabrication tolerances for the edge position on a part and the clarity and regularity of the edge line in the image. For example, if the expected fabrication tolerance is small, and the expected or observed clarity and regularity of the edge line in the image are good, then the confidence value for the edge location is set at a high level, indicating that the edge location should be a dominant factor in determining a desirable lighting vector. Conversely, if the expected fabrication tolerance is crude, and the expected or observed clarity and regularity of the edge line in the image are poor due to material transparency, rough surface finish, large edge radius, or the like, then the confidence value for the edge location is set at a low level, indicating that the edge location is a poor factor for determining a desirable lighting vector. As explained further below, the confidence value is used according to the systems and methods of this invention to determine whether the associated type of image result, that is, the edge location in this case, is expected to have good reliability as an image result and should be accorded high importance in determining a desirable lighting configuration, or poor reliability as an image result and should be accorded lower importance in determining a desirable lighting configuration. In various exemplary embodiments, the start-up confidence value for the edge location is set by the operator of the vision system by input to an edge tool user interface, or by manually or automatically indicating various points along the edge through a suitable user interface and operating the vision system to determine the quality of a best fit to the points, or based on the CAD data operations of step S2030. Use of the confidence value for the edge location in various exemplary embodiments according the systems and methods of this invention is described in detail further below. Operation the continues with step S2076.

In step 2076 any additional "non-edge" analysis parameters which are useful for the purpose of determining a desirable lighting vector for the current operation are set. For example, surface height determination and surface finish determination are enhanced by proper lighting. In such a case, suitable analysis parameters such as confidence values related to the surface height determination and surface finish determination, as well as other analysis parameters will be apparent to one skilled in the art, may be used according to various embodiments of the systems and methods according to this invention. Operation then proceeds to step S2077, where operation returns to step S2080.

Figure 7:
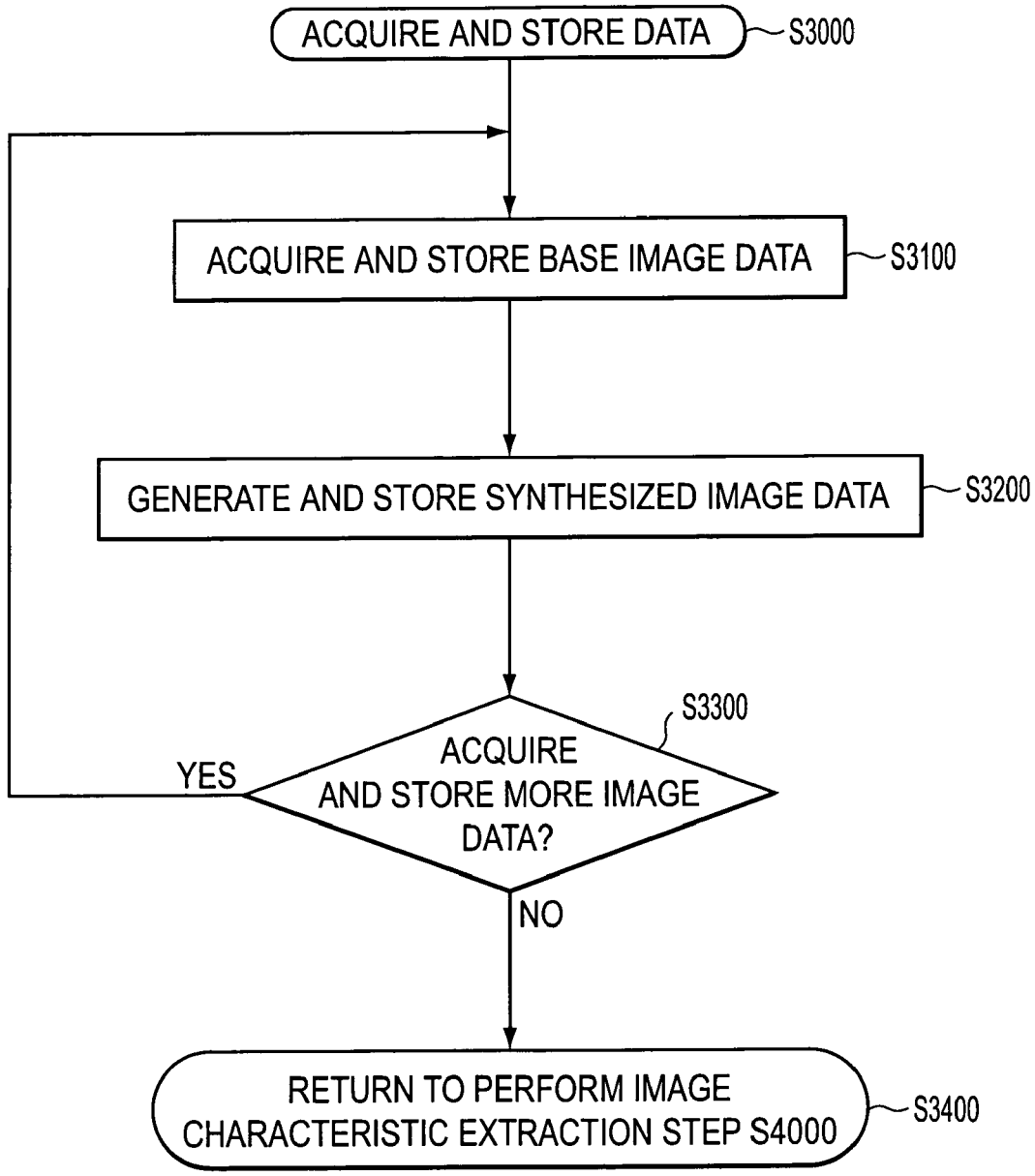
FIG. 7 is a flowchart outlining in greater detail one exemplary embodiment of a method for acquiring and storing data of the object to be viewed according to this invention.

FIG. 7 is a flowchart outlining in greater detail one exemplary embodiment of a method for acquiring and storing the image data to be used in accordance with this invention of step S3000. Beginning in step S3000, operation proceeds to step S3100, where base image data is acquired and stored. Base image data, is, in general, actual images that have been captured and stored using the vision system with a defined lighting vector corresponding to each base image. Then, in step S3200, synthesized image data is generated, or acquired, and stored. The synthesized images can be generated, for example, by combining two or more of the base images to create a synthesized image. Next, in step S3300, a determination is made whether more image data needs to be acquired and stored. It should be appreciated that in various exemplary embodiments, iterations of the acquiring and generating steps S3100–S3200 are governed by the step S3300, in order to gather all the required lighting/image data. However, in other exemplary embodiments, the steps S3100 and S3200 may gather a sufficient or exhaustive set of data in one iteration. It should be appreciated that the step S3300 is not necessary in such other embodiments. If, in step S3300, more image data needs to be acquired and stored, then operation jumps back to step S3100. Otherwise, if no more image data is to be acquired and stored, then operation proceeds to step S3400, where operation returns to step S4000.

Figure 8:
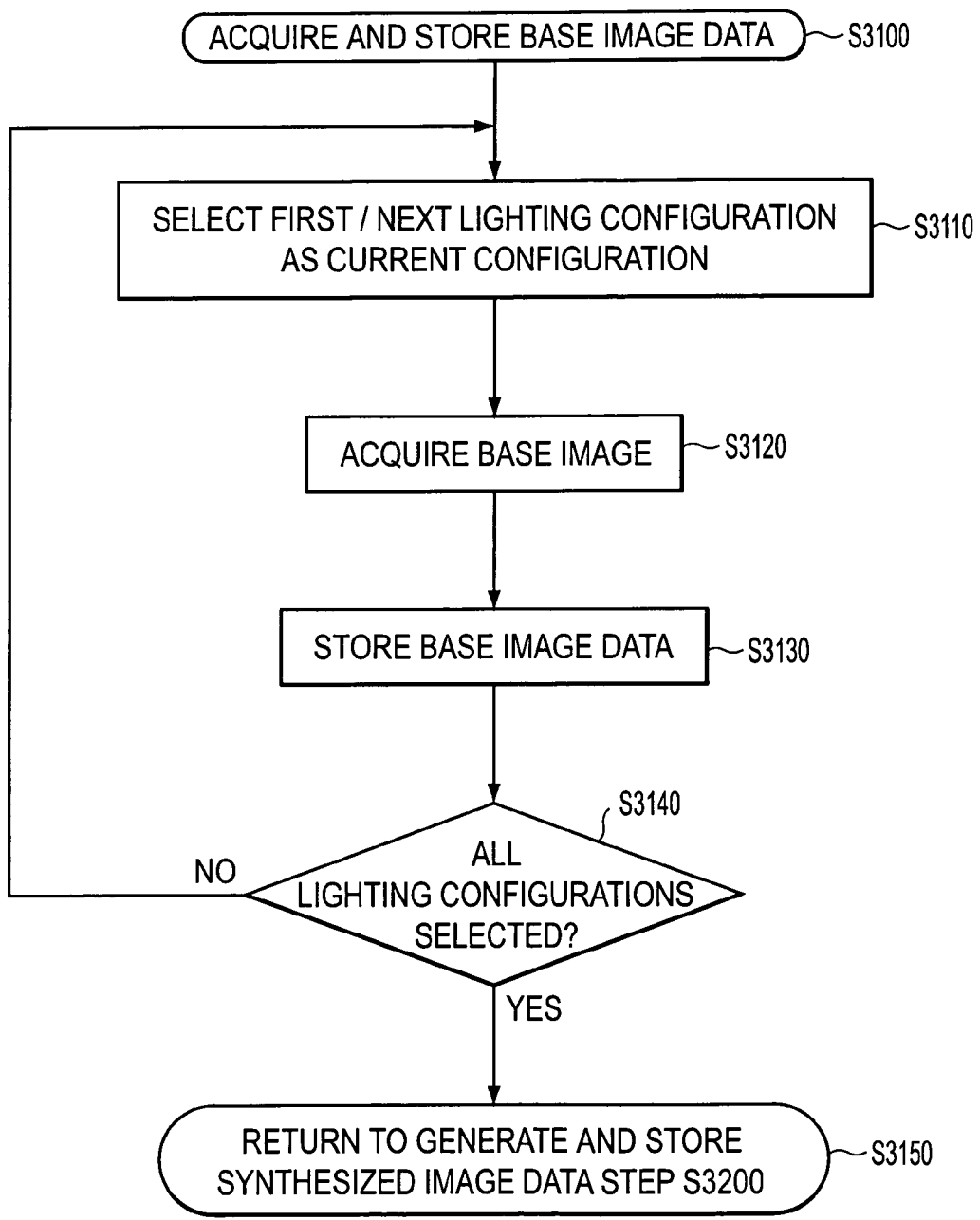
FIG. 8 is a flowchart outlining in greater detail one exemplary embodiment of a method for acquiring and storing base image data according to this invention.

FIG. 8 is a flowchart outlining in greater detail one exemplary embodiment of the method for acquiring and storing base image data of step S3100. Beginning in step S3100, operation proceeds to step S3110, where the first or next lighting configuration, also referred to as a lighting vector, is selected as a current lighting configuration. As previously discussed with reference to the vision system shown in FIG. 1, each different lighting configuration includes a different setting for each of the light sources 115–118. In particular, each lighting configuration indicates whether each particular light source is on or off, and, if any light source or portion of the programmable ring light is on, the height of the programmable ring light above the stage 102. Next, in step S3120, a base image is acquired when the part 102 is illuminated according to the current lighting configuration. Then in step S3130, the acquired base image and corresponding lighting configuration is stored in memory. Operation then proceeds to step S3140.

In step S3140, a determination is made whether all of the desired actual lighting configurations have been selected and used to capture a corresponding base image. If, in step S3140, all of the desired lighting configurations have not been selected, then operation jumps back to step S3110, where the next lighting configuration is selected as the current lighting configuration. However, if, in step S3140, all of the desired lighting configurations have been selected, then operation proceeds jumps to step S3150, where operation returns to step S3200.

With respect to FIG. 8, it should be appreciated that in various exemplary embodiments, the desired actual lighting configurations are defined by any manual, semi-automatic or automatic method which is compatible with the vision system. In various exemplary embodiments, the desired actual lighting configurations are determined by an expert user or an expert program based on the anticipated type of image or image analysis to be performed. In further embodiments, the light settings in the desired actual lighting configurations are generally chosen to provide full illumination, that is, so that the brightest pixels in the relevant portion of the image are at or near the saturation level. In various other exemplary embodiments, the desired actual lighting configurations are simply default configurations which gather a set of lighting/image data that allows the range of lighting configurations available for the system or for the type of part being imaged to be sufficiently or exhaustively characterized.

The inventors have determined that if a 4-quarant PRL is included in the system, it is generally advantageous to acquire base images with the PRL set at each of four heights over its operating height range. At each height, it is generally advantageous to acquire a base image with each quadrant light source separately, plus an image with all quadrants set to the same brightness, so that the entire PRL is treated as a single combined source. A single base image for each of a coaxial light and a stage light often is sufficient. Further considerations related to desirable actual lighting configurations are apparent throughout this description and in the incorporated 187 application.

Figure 9:
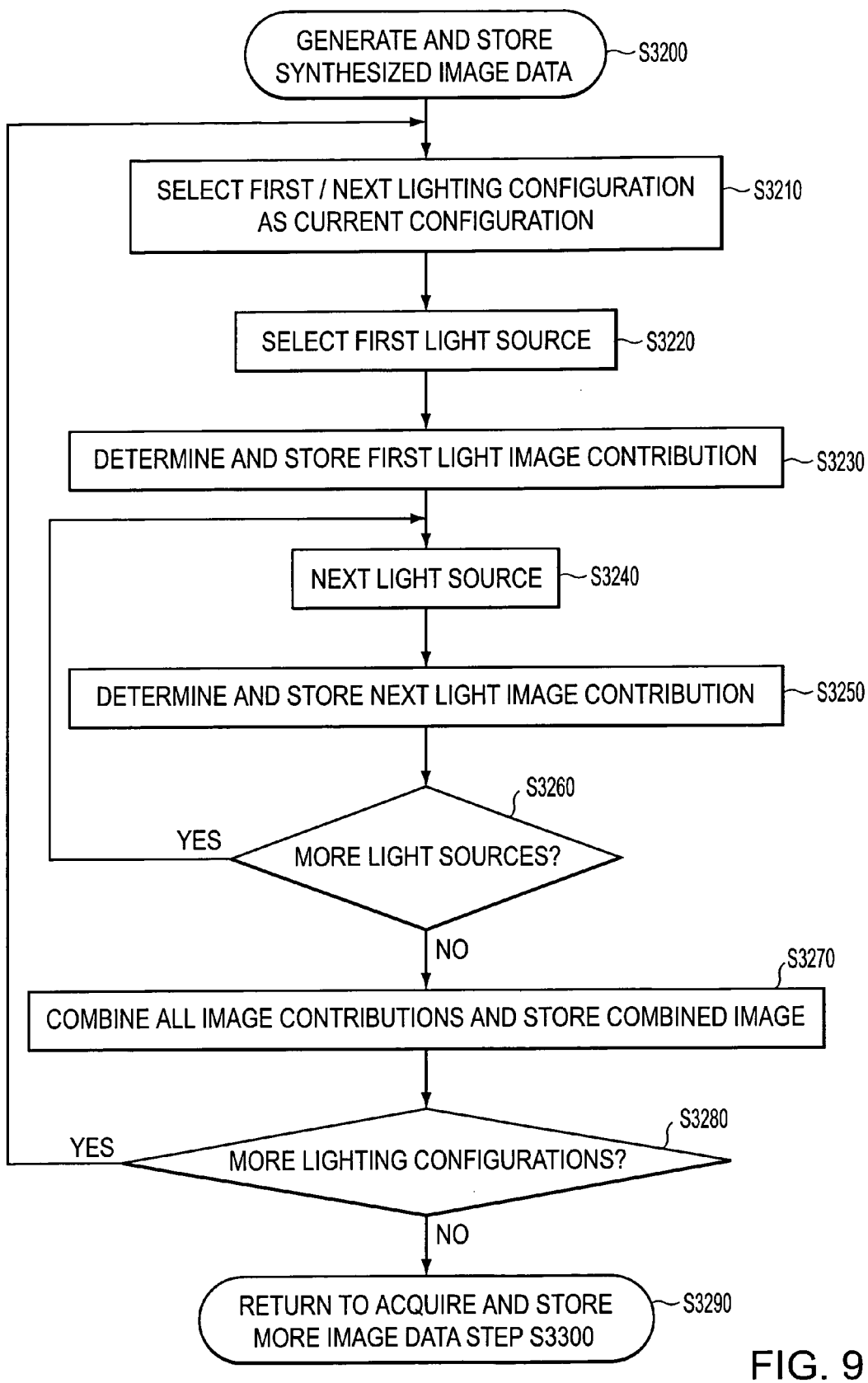
FIG. 9 is a flowchart outlining in greater detail one exemplary embodiment of a method for generating and storing synthesized image data according to this invention.

FIG. 9 is a flowchart outlining in greater detail one exemplary embodiment of the method for generating and storing synthesized image data of step S3200. Beginning in step S3200, operation proceeds to step S3210, where a first or next lighting configuration is selected as the current lighting configuration. Next, in step S3220, the first light source which is to be included in the synthesized image data is selected from the current lighting configuration. Operation then proceeds to step S3230.

In step S3230, the synthesized image contribution due to the first light source is determined. In various exemplary embodiments, the first light source is set at a synthetic level according to the first current lighting configuration. Then, a base image is identified wherein the contribution of the first light source to the base image pixel values is known. Then the contribution of the first light source to the synthetic image pixel values is determined by reducing or increasing the base image pixel values due to the first light source according to the proportion of the first light source's synthetic light level to its base image light level. Operation then proceeds to step S3240.

In step S3240 the next light source which is to be included in the synthesized image data is selected from the current lighting configuration. Operation then proceeds to step S3250.

In step S3250, the synthesized image contribution due to the next light source is determined. In various exemplary embodiments, the next light source is set at a synthetic level according to the next current lighting configuration. Then, a base image is identified wherein the contribution of the next light source to the base image pixel values is known. Then the contribution of the next light source to the synthetic image pixel values is determined by reducing or increasing the base image pixel values due to the next light source according to the proportion of the next light source's synthetic light level to its base image light level. Operation then proceeds to step S3260.

In step S3260, a determination is made whether all of the light sources included in the current configuration have been selected and their synthetic image contributions determined. If, in step S3260, all of the light sources have not been selected, then operation jumps back to step S3240, where the next light source is selected. However, if, in step S3260, all of the light sources in the current lighting configuration have been selected, then operation proceeds to step S3270, where the synthetic image contributions of all the light sources in the current lighting configuration are combined to create the corresponding synthetic image, and the result stored. Operation then proceeds to step S3280.

In step S3280, a determination is made whether all of the desired lighting configurations have been selected. If, in step S3260, all of the desired lighting configurations have not been selected, then operation returns to step S3210. If, in step S3280, all of the desired synthetic lighting configurations have been selected, operation proceeds to step S3290, where operation returns to the step S3300.

With respect to FIG. 9, it should be appreciated that in various exemplary embodiments, the desired synthesized lighting configurations are defined by any manual, semi-automatic or automatic method which is compatible with the vision system. In various exemplary embodiments, the desired synthesized lighting configurations are determined by an expert user or an expert program based on the anticipated type of image or image analysis to be performed. In further embodiments, the light settings in the desired synthesized lighting configurations are generally chosen to provide full illumination, that is, so that the brightest pixels in the relevant portion of the image are at or near the saturation level. For example, a first light source is set at a relatively low level, a second light source is set at a level expected to correspond to full illumination in the resulting synthetic image. To achieve full illumination, in various exemplary embodiments, the resulting synthetic image is determined based on appropriate base images, and if the resulting synthetic image is significantly saturated or under-exposed, then all the settings in the desired synthetic lighting configuration are scaled proportionally for appropriate full illumination. For further similar synthetic image lighting configurations, the first light is then synthetically increased by a chosen increment and the second light is then again synthetically set to a level that achieves full illumination.

In various other exemplary embodiments, to achieve full illumination, the base images corresponding to the contribution of each light source are each acquired at full illumination. Then, to approximate full illumination in each combined synthetic image, the settings corresponding to each source in each base image are divided by the number of base images which must be used to determine the combined synthetic image. Since the optical system and the camera are approximately linear until saturated, the resulting lighting configuration settings will correspond to a fully illuminated synthetic image for the combined sources.

In various other exemplary embodiments, the desired synthesized lighting configurations are simply default configurations which gather a set of lighting/image data that sufficiently or exhaustively characterizes the range of lighting configurations available for the system or for the type of part being imaged.

It should also be appreciated that when light sources within a PRL are combined according to a current lighting configuration, the base image(s) corresponding to each source should correspond to the same PRL height, as specified in the current lighting configuration. Furthermore, if a PRL configuration where all quadrants are illuminated is combined with another source in a current lighting configuration, and a base image is available where all PRL quadrants are simultaneously illuminated as described with respect to FIG. 8 above, then all PRL quadrants may be treated as a single light source when using that base image according to the operations of FIG. 9.

The inventors have determined that if a 4-quarant PRL, a coaxial light and a stage light are included in the system, in addition to the previously described base images, it is generally advantageous to acquire synthetic images with the PRL set at each of four heights over its operating height range. At each height, it is generally advantageous to acquire a synthetic image with each possible combination of two quadrant light sources set at the same brightness, and with each single quadrant combined with the coaxial light source. Further considerations related to desirable synthesized lighting configurations are apparent throughout this description and in the incorporated 187 application.

More generally, it should be appreciated that the incorporated 187 application includes alternative embodiments useable for the various base image acquiring and synthetic image acquiring operations of FIGS. 7–9, either separately or combination, as will be apparent to one skilled in the art.

Figure 10:
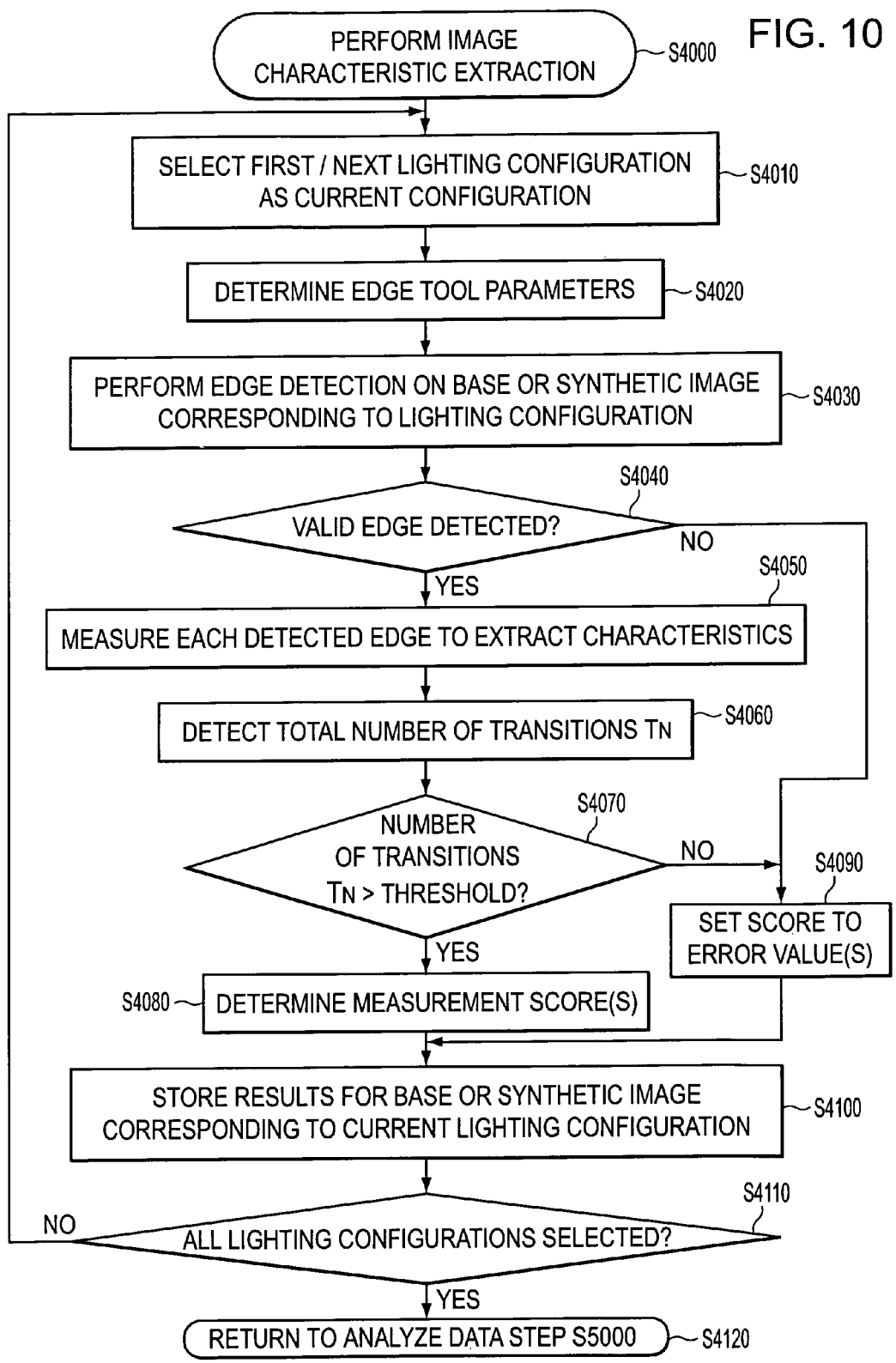
FIG. 10 is a flowchart outlining in greater detail one exemplary embodiment of a method for extracting one or more image characteristics according to this invention.

FIG. 10 is a flowchart outlining in greater detail one exemplary embodiment of the method for performing characteristic extraction of step S4000 in accordance with this invention. In particular, the exemplary embodiment of FIG. 10 extracts characteristics which are useful when setting the lighting configuration in relation to edge analysis operations. However, it should be appreciated that FIG. 10 illustrates just a few of an infinite number of different image characteristics that can be extracted from the base and synthetic images and used in the systems and method according to this invention. Thus, it should be understood that the particular steps outlined in FIG. 10 are illustrative only and should not be considered limiting of the scope of step S4000 of FIG. 4.

Beginning in step S4000, operation proceeds to step S4010, where a first/next one of the actual and synthetic lighting configurations is selected as the current lighting configuration. Then, in step S4020, one or more parameters for learning and/or running an edge analysis tool are determined or defined. In various exemplary embodiments, these parameters can be determined or defined using a dual area contrast tool such as that shown in FIG. 3, for example, in determining the standard deviations of the pixel intensities of two or more regions of interest near an edge, categorizing a largest and smallest standard deviation, and then setting the scanning direction based on the standard deviation results so that the process is performed from a smooth side of the image to a rough side of the image. In various other exemplary embodiments, step S4020 is analogous to and/or includes one or more of the operations described in relation to the steps S2072–S2075 of FIG. 6. Other exemplary parameters, as well as image analysis tools operable to perform various edge tool operations and dual-area contrast tool operations usable for characteristics extraction are also available in commercial vision machines and software, such as the Quick Vision series of vision inspection machines and QVPAK software available from Mitutoyo America Corporation (MAC), located in Aurora, Ill. Operation then proceeds to step S4030.

In step S4030, an edge detection is performed for the selected current lighting configuration and the parameters of steps S4010 and S4020. For example, in various exemplary embodiments, an edge tool is used to analyze the intensity profile of an edge for five separate scan lines across the edge in a "learn" mode of the tool. In step S4030, the edge detection can be performed to analyze and store, or "learn", various characteristics and/or features of the scan line intensity profiles which characterize the edge, so that the edge tool can be run automatically using the learned parameters. Various exemplary characteristics and/or features of the scan line intensity profiles include the intensity change across the edge, the direction of intensity increase across the edge, the number or proportion of scan lines across the edge that include intensity changes above a threshold value, and the like. In one exemplary embodiment, the mean value of each characteristics or feature is the value learned or stored as the basis for actual "run-time" edge measurements performed later. Operation then proceeds to step S4035.

In step S4040, it is determined whether the edge detection operation of step S4030 detected a valid edge. For example, the characterizations in step S4030 may indicate that the edge so "weak" that an edge measurement based on the image according to the current lighting configuration would be either impossible or too uncertain. If it is determined that a valid edge was not detected, then operation jumps to step S4090. Otherwise, operation proceeds to step S4050.

In step S4050, each detected edge is measured using the values learned in step S4030, in order to extract particular characteristics and/or values evaluated in other steps according to the systems and methods of this invention and described in further detail below. Then, operation proceeds to step S4060.

In step S4060, an exemplary image characteristic is extracted. Based on the results of steps S4020 and S4050, the total number, or proportion, $T_N$ of scan lines which exhibit intensity transitions indicative of a valid edge are determined. Operation then proceeds to step S4070.

In step S4070, a determination is made whether the number of transitions $T_N$ is greater than a predetermined threshold. If, in step S4070, the number of transitions $T_N$ detected exceeds the predetermined threshold ($T_N$>Threshold), then the edge measurements are considered valid. Accordingly, operation proceeds to step S4080. Otherwise, operation jumps to step S4090.

In step S4080, one or more additional image characteristics or measurement scores are determined. For example, a shape measurement score can be determined that indicates the deviation between a best fit line and the actual edge point data determined from the image. In various exemplary embodiments this operation uses information from step S2072 of FIG. 6. Alternatively or additionally, a position measurement score can be determined that indicates a deviation between actual edge point data determined from the image and an expected position using prior knowledge data. In various exemplary embodiments this operation uses information from step S2073 of FIG. 6. Further considerations related to additional image characteristics or measurement scores which may be included in the operations of step S4080 are apparent throughout this description and in the incorporated 187 application. Operation then continues to step S4100.

In contrast, in step S4090, because the image of the edge was determined to be invalid in an image acquired or generated using the current lighting configuration, the one or more measurement scores are set to error values which effectively exclude the current lighting configuration from consideration as a useful actual lighting configuration according the systems and methods of this invention. Operation then proceeds to step S4100 where the image characteristic values and/or measurement score results for the image are stored corresponding to the current lighting configuration.

Next, in step S4110, a determination is made whether all of the lighting configurations have been selected. If all lighting configurations have not been selected, operation jumps back to step S4010, where the next lighting configuration is selected. Otherwise, operation proceeds to step S4120, where operation returns to step S5000.

Figure 11:
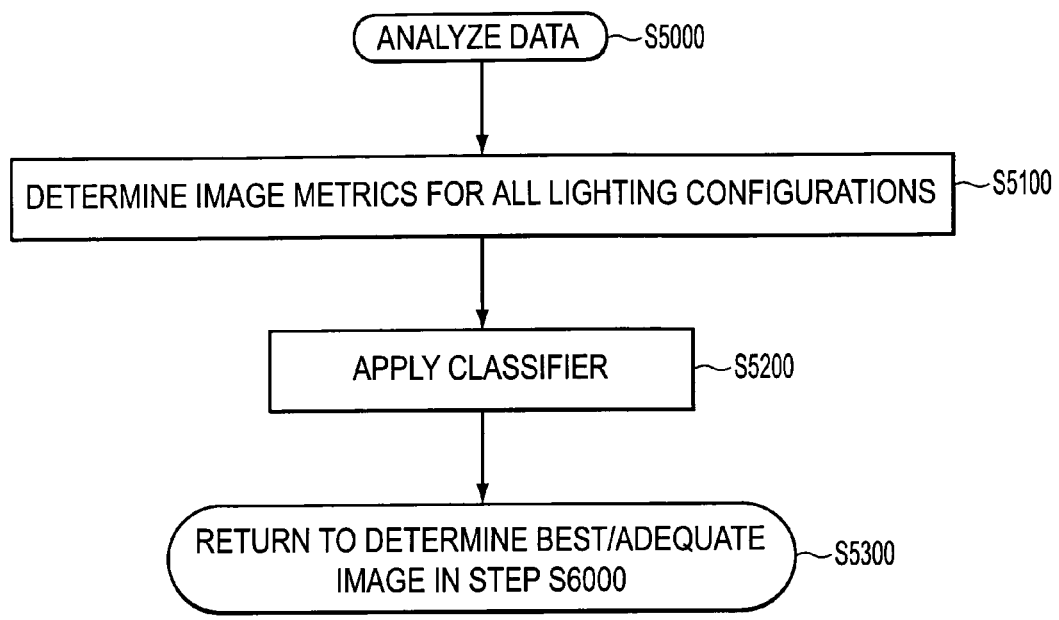
FIG. 11 is a flowchart outlining a first exemplary embodiment of a method for analyzing data according to this invention.
Figure 12:
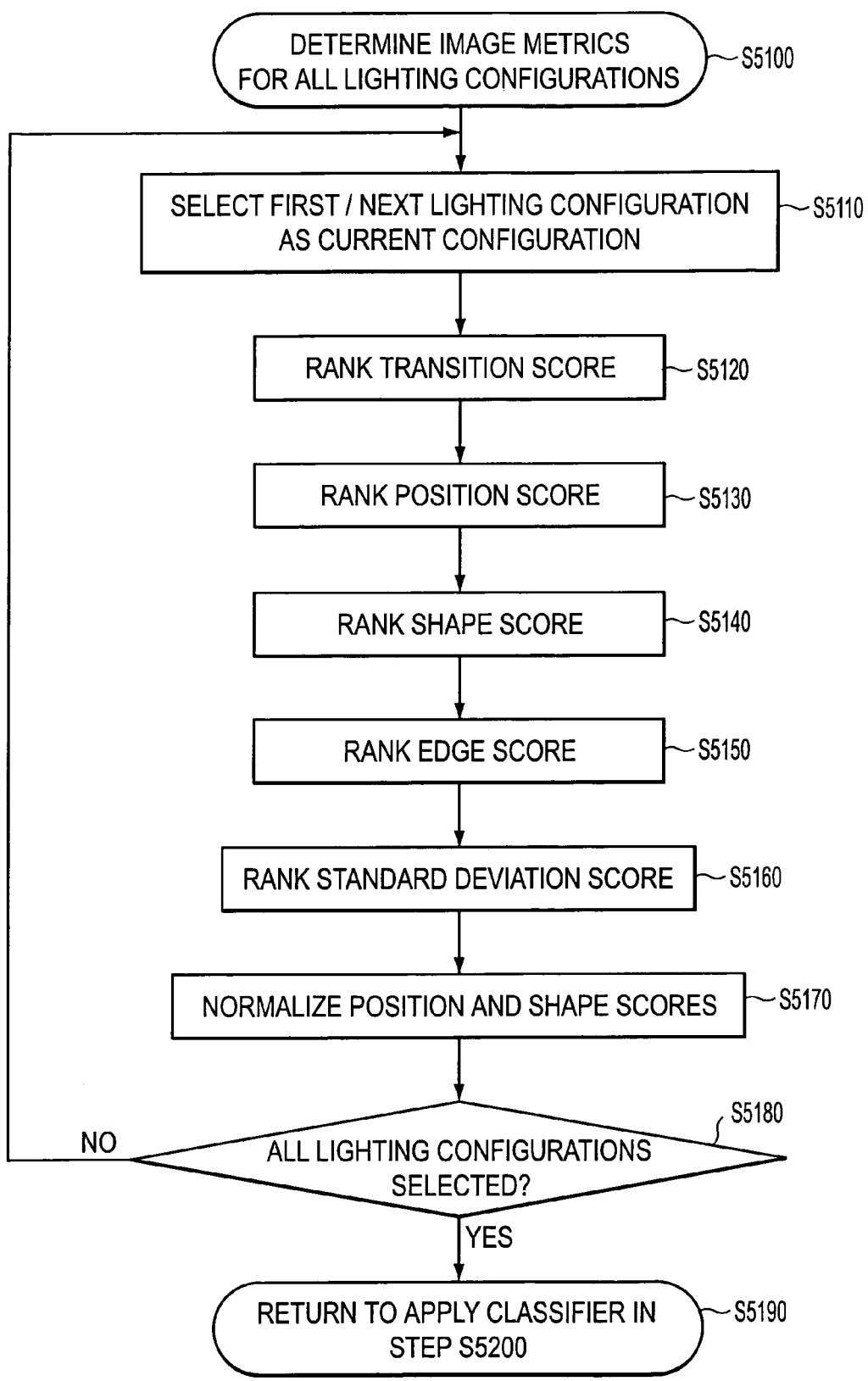
FIG. 12 is a flowchart outlining in greater detail one exemplary embodiment of a method for determining image metrics for all lighting configurations according to this invention.

FIG. 11 is a flowchart outlining in greater detail one exemplary embodiment of the method for analyzing data of step S5000. Beginning in step S5010, the image metrics are determined for each lighting configuration. A more detailed description of determining the image metrics is shown in FIG. 12. Then, in step S5200, a classifier is applied to the determined image metrics to determine a best image from the base and synthetic images. A more detailed description of the process for applying the classifier is discussed with reference to FIG. 13. Then, in step S5400, operation returns to step S6000.

FIG. 12 is a flowchart outlining in greater detail one exemplary embodiment of the method for determining image metrics for all lighting configurations of step S5100. Beginning in step S5100, the operation proceeds to step S5110 where a first/next lighting configuration is selected as the current lighting configuration. Next, in step S5120, an edge quality score for a lighting configuration is ranked compared to the edge quality score for other configurations. The edge quality score can be, for example, the transition score $T_N$ determined in step S4050. Next, in step S5130, a position score for a lighting configuration is ranked compared to the position score for other configurations. The position score can, for example, be the position measurement score discussed with respect to step S4080. Next, in step S5140, the shape score for a lighting configuration is ranked compared to the shape score for other configurations. The shape score can be, for example, be the shape measurement score discussed with respect to step S4080. Control then proceeds to step S5150.

In step S5150, an edge score for a lighting configuration is ranked compared to the edge score for other configurations. The edge score can, for example, be the magnitude of the predetermined threshold discussed with respect to step S4070. Then, in step S5160, a standard deviation score for a lighting configuration is ranked compared to the score for other configurations. Control then proceeds to step S5170.

In step S5170, the position score and shape score can be normalized relative to various rank scores of steps S5120–S5170, and in accordance with the design of the classifier used to determine the best lighting/image. Then, in step S5180, a determination is made as to whether all lighting configurations have been selected as the current configuration. If all lighting configurations have not been selected, then operation returns to step S5110 where the process is repeated for the next lighting configuration. The operation for determining the metrics for all lighting configurations can continuously update a internal list for all ranked images. For example, each time an image under a lighting configuration is ranked, the operation can automatically position the ranked image in sequenced order, i.e., rank from highest to lowest values, as compared to all of the other ranked images. If it is determined in step S5180 that all of the lighting configurations have been selected, the operation returns to step S5200 to apply the classifier.

It should be appreciated that FIG. 12 illustrates just one of an infinite number of methods for determining image metrics usable according to the systems and methods of this invention. In particular, the exemplary embodiment of FIG. 12 metrics which are applicable when setting the lighting configuration in relation to edge analysis operations. In addition, the metrics of FIG. 12 are usable either alone or in any combination, along with a corresponding classifier according to the systems and methods of this invention. Thus, it should be understood that the particular steps outlined in FIG. 12 are illustrative only and should not be considered limiting of the scope of step S5100 of FIG. 11.

Figure 13:
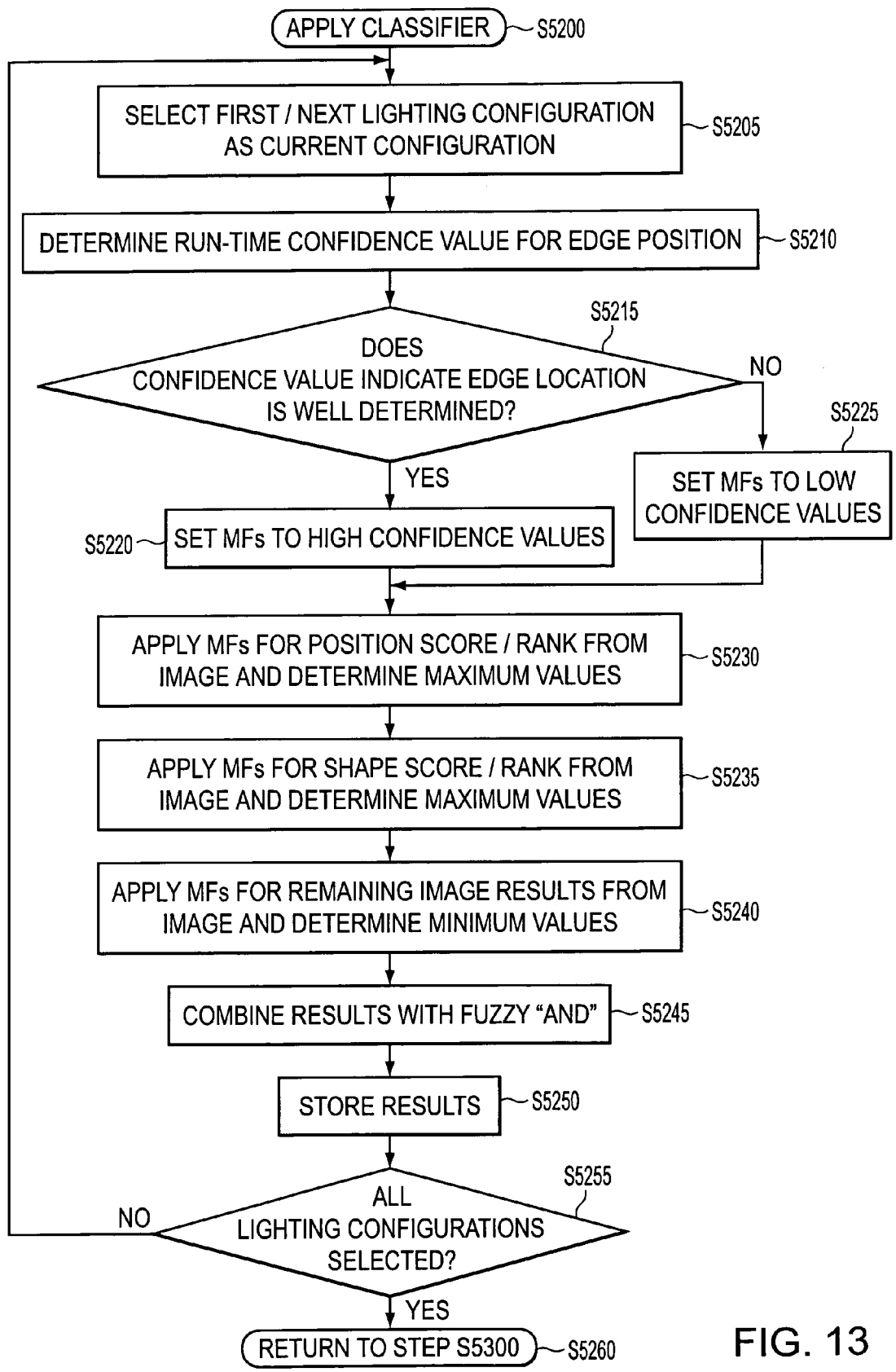
FIG. 13 is a flowchart outlining in greater detail one exemplary embodiment of a method for applying a classifier according to this invention.

FIG. 13 is a flowchart outlining in greater detail one exemplary embodiment of a method for applying a classifier in furtherance of determining the best image in accordance with this invention. In particular, an exemplary fuzzy classifier is described in FIG. 13.

Beginning in step S5200, operation proceeds to step S5205, where the first or next lighting configuration is selected as the current configuration. Then, in step S5210, a run-time confidence value is determined, if applicable. It should be appreciated that in some cases the start-up confidence value discussed with respect to step S2075 was based only on expectations for the edge image or a limited image analysis. In contrast, here it is possible to analyze all the base and synthetic image data or measurements to determine if the true character of the best edge image requires the confidence value assumed at start-up to be modified. If so, the confidence value is modified. However, it should be appreciated that in other exemplary embodiments and applications, the start-up confidence value may safely be assumed to be valid, and the step S5210 may be omitted. Operation then proceeds to step S5215.

In step S5215, a determination is made whether the current confidence score indicates that the edge location is well defined. If, in step S5215, the confidence score indicates a well defined edge, operation proceeds to step S5220, where the membership functions to be used by the classifier are set to a "high confidence" configuration appropriate for classifying images including a well-defined edge, and operation continues to step S5230. However, if, in step S5220, the confidence score does not indicate a well defined edge, operation proceeds to step S5225, where the membership functions to be used by the classifier are set to a "low confidence" configuration appropriate for classifying images including a poorly-defined edge and operation continues to step S5230.

In step S5230, membership functions for position score and position rank from each image are applied and the maximum value of the two is kept to represent the quality of the position characteristic. Then, in step S5235, membership functions for shape score and the shape rank from each image are applied and the maximum value of the two is kept to represent the quality of the shape characteristic. Operation then proceeds to step S5240.

Figure 15:
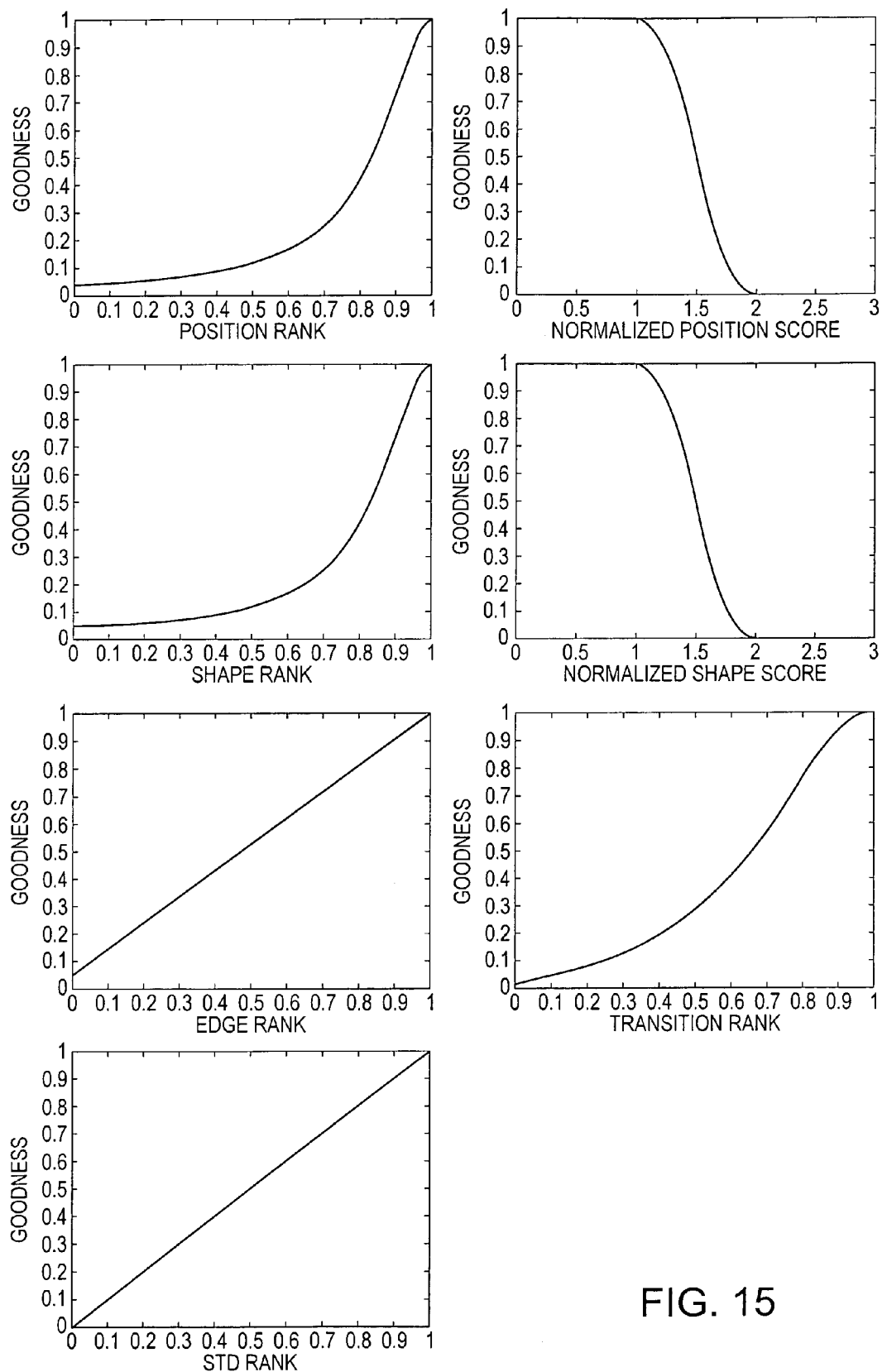
FIG. 15 shows various exemplary embodiments of membership functions usable in the systems and methods according to this invention.

In step 85240, membership functions are applied for any remaining metrics/image characteristics to obtain or determine the individual fuzzy classifier values that represent the relative importance of each metric/image feature. FIG. 15 shows various exemplary embodiments of membership functions that are usable in step S5240 to determine the fuzzy classifier values for various different types of scores or ranks. Next, in step S5245, an overall classifier value is determined for the current lighting configuration by combining the individual fuzzy classifier values obtained in steps S5230–5240 using a fuzzy "AND" operation. That is, the lighting configuration that has a set of image results including a close position score or a top edge rank, a close shape score or a top shape rank, a strong edge score, a low standard deviation score in at least one region of interest, and a large value of $T_N$, will be evaluated as corresponding to a favorable lighting configuration. Then, in step S5257, the results of the determined overall classifier value are stored. Operation then continues to step S5255.

In step S5255, a determination is made whether all lighting configurations have been selected. If, in step S5255, all lighting configurations have not been selected, operation returns to step S5205. If, in step S5255, all lighting configurations have been selected, operation proceeds to step S5260 where operation returns to step S5300.

With respect to the operations of steps S5220 and S5225, it should be appreciated that in various exemplary embodiments the membership functions associated with a high confidence value accord very strong weighting in the classifier to better position rank, better shape rank, close position scores, and close shape scores, because it is expected that at good edge image will appear at a reasonably precise location, with a precise shape when it is properly lighted. Conversely, these same factors are weighted more similarly to the other factors when the confidence value is low.

The inventors have found that classifiers including a set of most or all of the image results included in FIGS. 12–13 generally approximate or exceed the accuracy and robustness of an expert human vision system operator. However, it should also be appreciated that a classifier can be based on a set of one or more metrics/image features in various exemplary embodiments. For example, when the confidence value is high, a set consisting of the position rank alone may suffice for many applications. Thus, it should be understood that the particular steps outlined in FIG. 13 are illustrative only and should not be considered limiting of the scope of step S5200 of FIG. 11.

More generally, as the number of image results, such as metrics, scores, image characteristics and the like, used by the classifier is increased from one, the accuracy and/or robustness of the classifier increases greatly for the first few image results added to the classifier, and then more gradually as more image results are added. It should also be appreciated that although an exemplary process of step 5200 has been shown using an exemplary fuzzy classifier, alternative fuzzy classifiers, neural classifiers, a hidden mark-up model or any other technique or algorithm known or later-developed can also be used as the classifier of step S5200, in furtherance of selecting the best image and corresponding lighting configuration in accordance with this invention. Furthermore, when another type of classification or evaluation is performed, it should be appreciated that the membership function operations described above may be replaced by any other appropriate operations for applying weighting factors to various image results in order to accord them greater or lesser relative importance in the classification or evaluation operations, and appropriate weighting operations are generally be apparent from or included in many well known classification or evaluation methods.

Furthermore, although various exemplary embodiments of the systems and methods according to this invention are described herein as determining or extracting image characteristics, determining measurement scores, and determining image metrics usable to evaluate and compare various actual and synthetic images, it should be appreciated that these terms are not mutually exclusive in various embodiments according of the systems and methods according to this invention. For example, a particular determined image characteristic may also operate as, or be derivable from, a related measurement score or image metric. Similarly, a particular measurement score may operate as, or be derivable from, a related image characteristic or image metric, and a particular image metric may also operate as, or be derivable from, a related measurement score or image characteristic, in various embodiments. Thus, these terms have been used in various contexts herein for the purpose of describing of various operations, but are not intentionally used in a mutually exclusive sense. More generally, any of these terms, their underlying data, or alternative data representations, whether derived from a single image or based on a rank or comparison between images, constitute one or more image results usable to determine whether a particular lighting configuration provides a best or adequate image according to the systems and methods of this invention.

Figure 14:
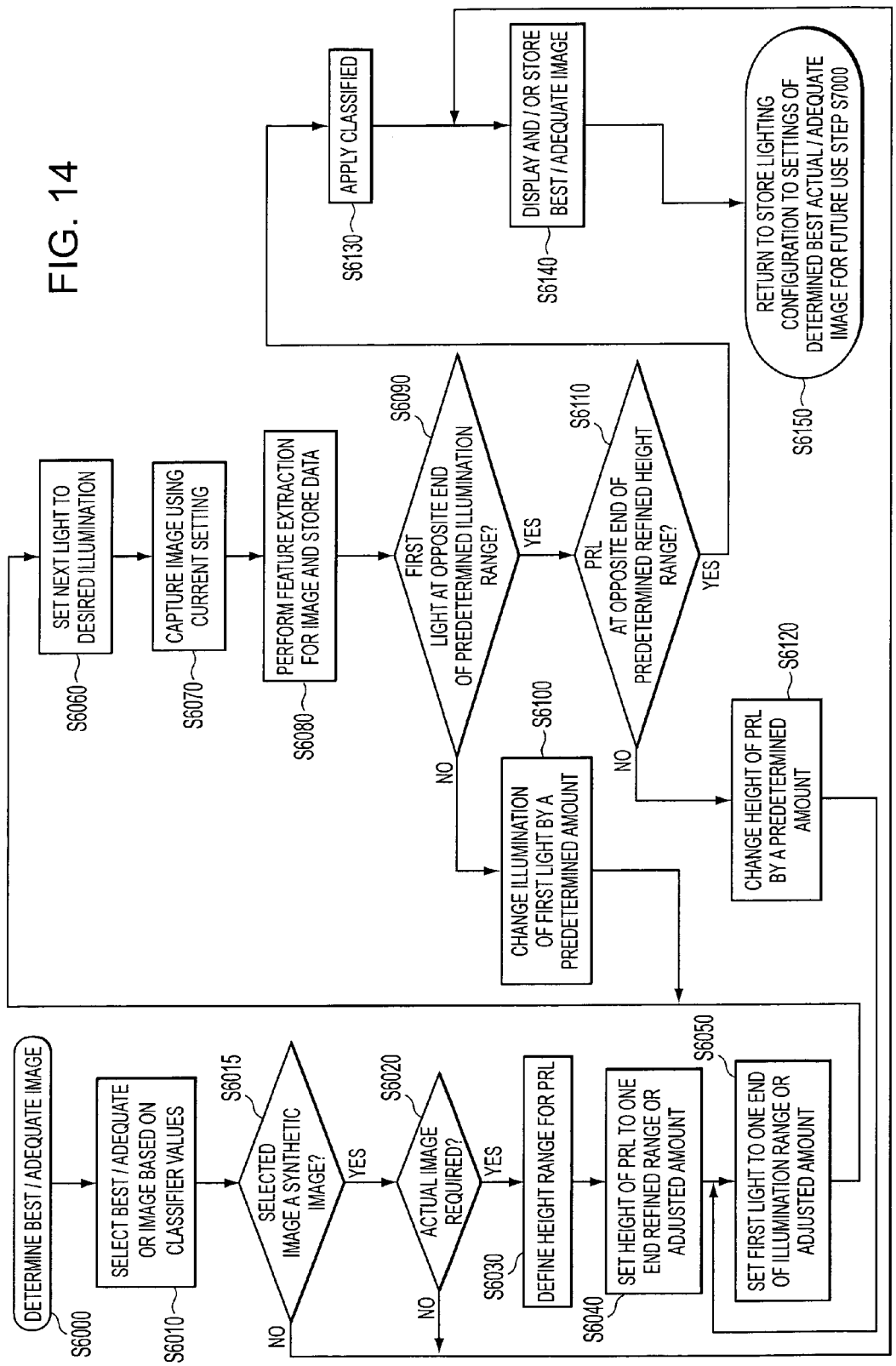
FIG. 14 is a flowchart outlining in greater detail one exemplary embodiment of the method for determining the best actual image according to this invention.

FIG. 14 is a flowchart outlining in greater detail one exemplary embodiment of the method for determining the best image from the base and synthetic images of step S6000. Since image characteristics can be very sensitive to angle of incidence of lighting from a PRL, the exemplary embodiment of FIG. 14 assumes that the lighting configuration of the best image includes a PRL light source and emphasizes refinement of the PRL lighting configuration. After beginning in step S6000, control proceeds to step S6010, where the best base or synthetic image determined in step S3000 is selected based on the image with the highest value determined by the classifier of step S5200. Alternatively, in various embodiments, a first adequate base or synthetic image may be selected by as described further below.

Next, in step S6015, a determination is made whether the selected best/adequate image is a synthetic image. If, in step S6015, the determined best image is not a synthetic image, i.e., it is an actual image, then operation proceeds directly to step S6140, where the actual image is displayed. However, if, in step S6015, the selected best/adequate image is a synthetic image, then operation proceeds to step S6020.

Next, in step S6020, a determination is made whether an actual image is required as the basis for the desired lighting vector. For example, an actual image may be required any time it is desired to confirm a synthetic lighting configuration before it is stored for repeated future use. As a further example, when the synthetic lighting configuration includes a PRL light source, the image characteristics can be very sensitive to the angle of incidence of lighting from a PR, and a refinement/optimization of the PRL settings based on actual images may be selected by the vision system user. If, in step S6020, an actual image is not required, then operation proceeds directly to step S6140, where the synthetic image displayed or stored in various embodiments. However, if, in step S6020, an actual image is required, then operation proceeds to step S6030.

In step S6030, a refined height range for the programmable ring light is determined based on the height of the programmable ring light for the lighting configuration of the determined best synthetic image. Then, in step S6040, the programmable ring light is set to a height equal to one end of the refined height range. Next, in step S6050, first one of the light sources used for the determined best synthetic image is set to one end of its illumination range. Then, in step S6060, one or more next light sources used for the determined best synthetic image is/are set to a desired illumination. In various exemplary embodiments, the light sources are set to achieve full illumination, as described elsewhere herein. Operation then proceeds to step S6070.

In step S6070, a base image is captured using the illumination setting determined in steps S6040–S6060 to illuminate the part 102. Then, in step S6080, one or more characteristics are extracted from the captured base image using the operation of step S4000, and stored. That is, the characteristic extraction process performed in step S6080 is the same characteristic extraction process shown in FIG. 10. Next, in step S6090, a determination is made whether the first light source is at the opposite end of the its illumination range. If, in step S6090, the first light is not at the opposite end of its illumination range, operation proceeds to step S6100. Otherwise, in step S6090, if the first light is at the opposite end of its illumination range, operation jumps to step S6110. In step S6100, the illumination setting of the first light source is changed by a predetermined amount. Operation then jumps back to step S6060. In contrast, in step S6110, a determination is made whether the height of the programmable ring light is at the opposite end of the refined height range. If, in step S6110, the programmable ring light is not at the opposite end of the refined height range, then operation proceeds to step S6120 and the height of the programmable ring light is changed within the refined height range. Operation then jumps back to step S6060. Otherwise, in step S6110, if the programmable ring light is at the opposite end of the refined height range, then operation continues to step S6130.

In step S6130, the classifier is applied to the new series of base images captured and analyzed in steps S6010–S6120. The classifier process used in step S6130 is the same used in step S5200. Next, in step S6140, if it useful in a particular application, the best base image, corresponding to the best lighting configuration determined by the classifier from the new series of base images, is displayed. Then, in step S6150, operation returns to step S7000 where the lighting configuration/vector settings corresponding to the best actual base image are stored for future use.

With regard to exemplary embodiment of step S6000 shown in FIG. 14, it should be appreciated that in various exemplary embodiments described herein, the contributions of light sources combined in a synthetic images are set at equal levels. The operations of FIG. 14 relax that constraint, allowing a better actual image and corresponding lighting configuration to be determined in some cases. However, in other exemplary embodiments of the step S6000, and particularly when a height-adjustable PRL is not included in the vision system lighting, a best or adequate actual image may be determined or confirmed simply by acquiring an actual image according to the best synthetic image lighting configuration and confirming that its overall classifier score is the best of all the actual images.

It should also be appreciated that although the foregoing detailed descriptions generally identify the best lighting configuration, to save processing time it is also within the scope of this invention to establish a set of image results or an overall classifier score threshold which is known to correspond to an adequate image for one or more image processing operations, and to stop the process at any point where it is indicated that a lighting configuration corresponds to a set of image results or an overall classifier score which is above the threshold. The set of image results or corresponding overall classifier score may be determined, for example, based on extensive vision lighting experience, according to the type of feature to be inspected and/or the configuration of the workpiece, or based on preliminary image results obtained from a crudely or approximately illuminated preliminary actual image acquired. Furthermore, it is also within the scope of this invention to suspend further processing of any lighting configuration at any point where it may be determined that the configuration will predictably fail to achieve the established overall classifier score threshold or where the configuration actually or predictably fails to be the best lighting configuration.

In FIG. 1, the control system portion 120 is, in various exemplary embodiments, implemented using a programmed general purpose computer. However, the control system portion 120 can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device, capable of implementing a finite state machine that is in turn capable of implementing the flowcharts shown in FIGS. 4–14 can be used to implement the control system portion 120.

Moreover, in FIG. 1, alterable portions of the memory 140 are, in various exemplary embodiments, implemented using static or dynamic RAM. However, the memory 140 can also be implemented using a floppy disk and disk drive, a writeable optical disk and disk drive, a hard drive, flash memory or the like. In FIG. 1, the generally static portions of the memory 140 are, in various exemplary embodiments, implemented using ROM. However, the static portions can also be implemented using other non-volatile memory, such as PROM, EPROM, EEPROM, an optical ROM disk, such as a CD-ROM or DVD-ROM, and disk drive, flash memory or other alterable memory, as indicated above, or the like.

Thus, in FIG. 1, the memory 140 can be implemented using any appropriate combination of alterable, volatile or non-volatile memory or non-alterable, or fixed, memory. The alterable memory, whether volatile or non-volatile, can be implemented using any one or more of static or dynamic RAM, a floppy disk and disk drive, a writeable or rewriteable optical disk and disk drive, a hard drive, flash memory or the like. Similarly, the non-alterable or fixed memory can be implemented using any one or more of ROM, PROM, EPROM, EEPROM, an optical ROM disk, such as a CD-ROM or DVD-ROM disk, and disk drive or the like.

It should also be understood that each of the circuits of the control system portion 120 shown in FIG. 1 can be implemented as portions of a suitably programmed general purpose computer. Alternatively, each of the circuits shown in the control system portion 120 of FIG. 1 can be implemented as physically distinct hardware circuits within an ASIC, or using a FPGA, a PDL, a PLA or a PAL, or using discrete logic elements or discrete circuit elements. The particular form each of the circuits shown in the control system portion 120 of FIG. 1 will take is a design choice and will be obvious and predictable to those skilled in the art.

Moreover, the control system portion 120 can be implemented as software executing on a programmed general purpose computer, a special purpose computer, a microprocessor or the like. In this case, the control system portion 120 can be implemented as a routine embedded in the vision system 100, as a resource residing on a server, or the like. The control system portion 120 can also be implemented by physically incorporating it into a software and/or hardware system.

While the invention has been described with reference to what are preferred embodiments thereof, it is to be understood that the invention is not limited to the preferred embodiments or constructions. To the contrary, the invention is intended to cover various modifications and equivalent arrangements. In addition, while the various elements of the preferred embodiments are shown in various combinations and configurations, which are exemplary, other combinations and configurations, including more, less or only a single element, are also within the spirit and scope of the invention.

What is claimed is:

1. A method for determining a desired lighting configuration for a vision system comprising a controllable lighting system and an imaging system, the desired lighting configuration usable to obtain a desirable image of at least one feature of a workpiece, the method comprising:

obtaining a plurality of base images of the at least one feature, each base image corresponding to an actual lighting configuration and comprising an actual image;

determining a set of at least one image result for at least one actual lighting configuration;

determining a set of at least one image result for at least one synthetic lighting configuration, each set of at least one image result based on the corresponding synthetic lighting configuration and at least one base image; and determining a desired lighting configuration based on the sets of image results.

2. The method of claim 1, wherein the step of determining the desired lighting configuration comprises selecting one of an actual and a synthetic lighting configuration based on the corresponding set of at least one image result.

3. The method of claim 2, wherein the selection is based on comparing the corresponding set of at least one image result to at least one other set of at least one image result.

4. The method of claim 3, wherein the at least one other set of at least one image result comprises an image result corresponding to an adequate image.

5. The method of claim 4, wherein the at least one other set of at least one image result corresponds to the image results of at least one other of the actual and synthetic lighting configurations.

6. The method of claim 5, wherein selecting one of an actual and a synthetic lighting configuration based on the corresponding set of at least one image result comprises selecting the one of an actual and a synthetic lighting configuration corresponding to the best set of at least one image result.

7. The method of claim 3, wherein the set of at least one image result comprises a plurality of image results, and comparing the corresponding set of image results to at least one other set of image results comprises:

evaluating each set of compared image results to determine an overall result for each set; and comparing the overall results.

8. The method of claim 7, wherein evaluating each set of compared image results to determine an overall result comprises according a relative importance to different types of image results included in the plurality of image results in determining the overall result.

9. The method of claim 8, wherein the according a relative importance to different types of image results further comprises according a first combination of relative importance when a particular type of image result is determined to have good reliability and the according a second combination of relative importance when the particular type of image result is determined to have poor reliability.

10. The method of claim 8, wherein the according a relative importance to different types of image results further comprises applying a weighting factor to at least one type of image result.

11. The method of claim 10, wherein each weighting factor is determined based on a membership function.

12. The method of claim 11, wherein the evaluation includes using fuzzy logic to determine the overall result.

13. The method of claim 2, wherein when the synthetic lighting configuration is selected, the step of determining the desired lighting configuration further comprises:
   determining at least one additional actual lighting configuration based on the selected synthetic lighting configuration;
   obtaining at least one additional actual image corresponding to the at least one additional actual lighting configuration;
   determining a set of at least one image result for each at least one additional actual lighting configuration;
   identifying the best set of image results, considering at least each set of image results corresponding to an additional actual lighting configuration; and
   determining the desired lighting configuration to be the lighting configuration corresponding to the best set of image results.

14. The method of claim 13, wherein the controllable lighting system further comprises a programmable ring light having at least one controllable source and a controllable height, wherein the at least one additional actual lighting configuration further comprises additional actual lighting configurations wherein the programmable ring light height is set to at least two settings over a refined range spanning the height setting in the selected synthetic lighting configuration, and the intensity setting of each programmable ring light source included in the synthetic lighting configuration is set to at least two levels for each height setting.

15. The method of claim 1, wherein the at least one image result comprises at least one of an edge position, an edge position score, an edge position rank, an edge shape, an edge shape score, an edge shape rank, an edge quality, an edge quality score, an edge quality rank, an edge strength, an edge strength score, an edge strength rank, a surface position, a surface position score, a surface position rank, a surface brightness, a surface standard deviation, a surface standard deviation score, and a surface standard deviation rank.

16. The method of claim 1, wherein the vision system further comprises at least one image analysis tool, wherein at least one image result is determined based on the operation of the image analysis tool.

17. The method of claim 1, wherein at least one of an actual lighting configuration and a synthetic lighting configuration is intended to correspond to full illumination.

18. The method of claim 17, wherein each actual and synthetic lighting configuration is intended to correspond to full illumination, and wherein basing a set of at least one image result on the corresponding synthetic lighting configuration and at least one base image at least comprises:
   selecting at least two base images, the at least two base images together including illumination from all the light sources included in the synthetic lighting configuration;
   dividing the pixel intensities of each base image by the number of selected base images;
   summing the divided pixel intensities for corresponding pixels in the selected base images; and
   basing the set of at least one image result on the summed pixel intensities.

19. A recording medium that stores a control program, the control program executable on a computing device, the computing device couplable to a vision system, the control program including instructions for determining a desired lighting configuration for a vision system having a controllable lighting system, the desired lighting configuration usable to obtain a desirable image of at least one feature of a workpiece, the instructions comprising:
   instructions for obtaining a plurality of base images of the at least one feature, each base image corresponding to an actual lighting configuration and comprising an actual image;
   instructions for determining a set of at least one image result for at least one actual lighting configuration;
   instructions for determining a set of at least one image result for at least one synthetic lighting configuration, each set of at least one image result based on the corresponding synthetic lighting configuration and at least one base image; and
   instructions for determining a desired lighting configuration based on the sets of image results.

20. An encoded signal that is transmitted and includes a control program to a device for executing the control program, the device couplable to a vision system, the control program including instructions for determining a desired lighting configuration for a vision system having a controllable lighting system, the desired lighting configuration usable to obtain a desirable image of at least one feature of a workpiece, the instructions comprising:
   instructions for obtaining a plurality of base images of the at least one feature, each base image corresponding to an actual lighting configuration and comprising an actual image;
   instructions for determining a set of at least one image result for at least one actual lighting configuration;
   instructions for determining a set of at least one image result for at least one synthetic lighting configuration, each set of at least one image result based on the corresponding synthetic lighting configuration and at least one base image; and
   instructions for determining a desired lighting configuration based on the sets of image results.

21. A vision system comprising:
   a controllable lighting system;
   an imaging system; and
   a light intensity control system that determines a desired lighting configuration for the controllable lighting system to obtain a desirable image of at least one feature of a workpiece using the imaging system, the desired lighting configuration determined based on at least one set of actual image results corresponding an actual lighting configuration and at least one set of simulated image results corresponding to a synthetic lighting configuration, the desired lighting configuration being one of the actual and simulated lighting configurations that corresponds to a set of image results chosen by comparison to at least one other set of image results.

22. The vision system of claim 21, wherein the at least one other set of image result comprises at least one of an adequate set of image results and a set of image results corresponding to one of the other actual and synthetic lighting configurations.

23. The vision system of claim 21, wherein the chosen image result is the best available image result.

24. The vision system of claim 21, wherein the at least one simulated image result is based on the corresponding synthetic lighting configuration and at least two actual images, the at least two actual images together including illumination from all the light sources included in the synthetic lighting configuration.

25. The vision system of claim 24, wherein at least one actual and synthetic lighting configuration is intended to correspond to full illumination.

26. The vision system of claim 21, wherein each compared set of image results is evaluated to determine an overall image result for the set, and the comparison is based on the overall result.

27. The vision system of claim 21, wherein the vision system operates at least partially automatically to determine the desired lighting configuration.

28. The vision system of claim 21, wherein:
the light intensity control system is part of a general computerized control system of the vision system, the general computerized control system further comprising a control instruction generation system;
the light intensity control system is operable by the control instruction generation system; and
the control instruction generation system generates at least one of a part program, an inspection program control instruction, and a controllable lighting system control instruction based on the desired lighting configuration determined by the light intensity control system.

29. The vision system of claim 28, wherein:
the control instruction generation system includes at least one image analysis tool, and at least one image result is determined based on the operation of the image analysis tool.

30. The vision system of claim 21, wherein the controllable lighting system comprises at least two of a stage light, a coaxial light, a ring light and a programmable ring light.

* * * * *